US008283630B2

(12) United States Patent
Miyamoto et al.

(10) Patent No.: US 8,283,630 B2
(45) Date of Patent: Oct. 9, 2012

(54) METHOD AND APPARATUS FOR MEASURING DIMENSION OF CIRCUIT PATTERN FORMED ON SUBSTRATE BY USING SCANNING ELECTRON MICROSCOPE

(75) Inventors: Atsushi Miyamoto, Yokohama (JP); Tomofumi Nishiura, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 58 days.

(21) Appl. No.: 13/024,594

(22) Filed: Feb. 10, 2011

(65) Prior Publication Data

US 2011/0127429 A1    Jun. 2, 2011

Related U.S. Application Data

(63) Continuation of application No. 12/354,923, filed on Jan. 16, 2009, now Pat. No. 7,888,638.

(30) Foreign Application Priority Data

Mar. 31, 2008    (JP) ................................. 2008-089131

(51) Int. Cl.
*G01N 23/00*    (2006.01)
*G21K 7/00*    (2006.01)

(52) U.S. Cl. ......... 250/307; 250/310; 250/311; 716/19; 716/20; 716/21; 702/155; 382/144; 382/145; 382/128; 382/199; 382/181

(58) Field of Classification Search .................. 250/307, 250/310–311; 716/19–21; 702/155; 382/144, 382/145, 128, 199, 181
See application file for complete search history.

(56) References Cited

U.S. PATENT DOCUMENTS

2006/0288325 A1* 12/2006 Miyamoto et al. .............. 716/19
2008/0159609 A1*  7/2008 Miyamoto et al. ............ 382/128

FOREIGN PATENT DOCUMENTS

JP    2002-328015    11/2002
JP    2007-250528     9/2007

* cited by examiner

*Primary Examiner* — Jack Berman
*Assistant Examiner* — Meenakshi Sahu
(74) *Attorney, Agent, or Firm* — Antonelli, Terry, Stout & Kraus, LLP.

(57) ABSTRACT

In the dimension measurement of a circuit pattern using a scanning electron microscope (SEM), in order to make it possible to automatically image desired evaluation points (EPs) on a sample, and automatically measure the circuit pattern formed at the evaluation points, according to the present invention, in the dimension measurement of a circuit pattern using a scanning electron microscope (SEM), it is arranged that coordinate data of the EP and design data of the circuit pattern including the EP are used as an input, creation of a dimension measurement cursor for measuring the pattern existing in the EP and selection or setting of the dimension measurement method are automatically performed based on the EP coordinate data and the design data to automatically create a recipe, and automatic imaging/measurement is performed using the recipe.

2 Claims, 15 Drawing Sheets

FIG. 6D

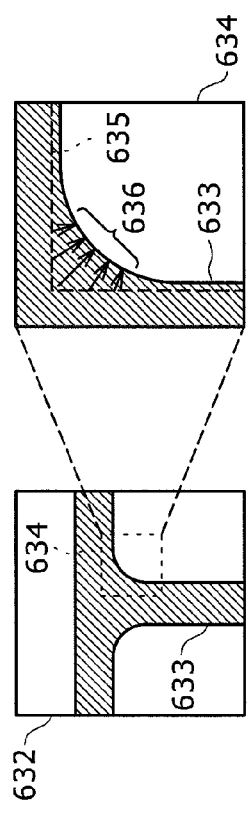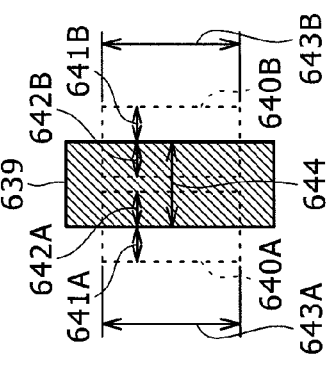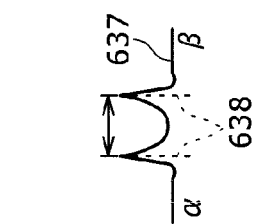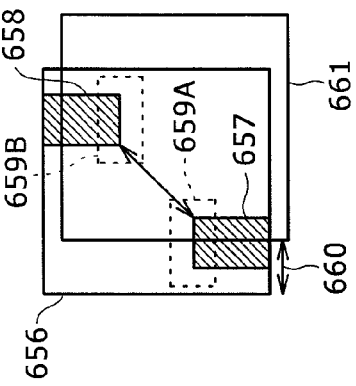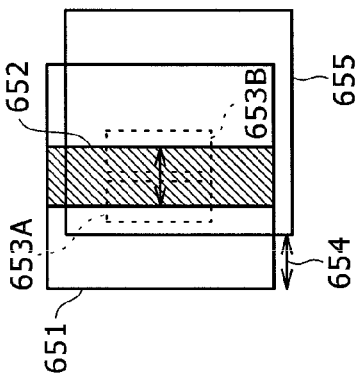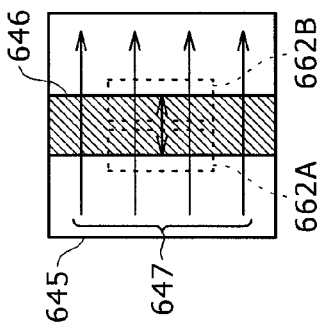

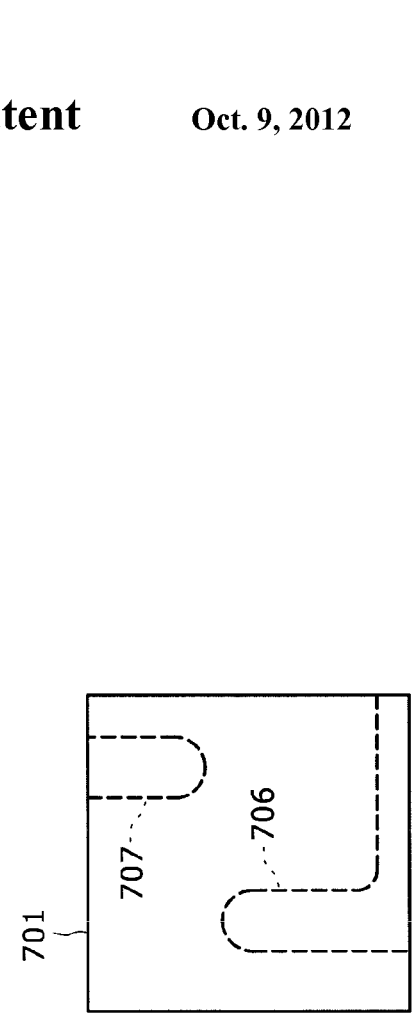
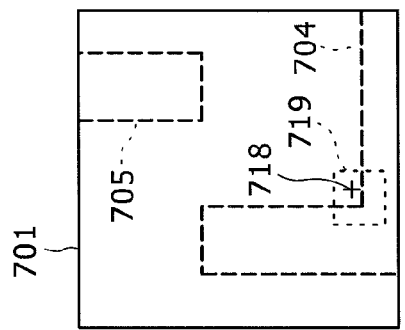
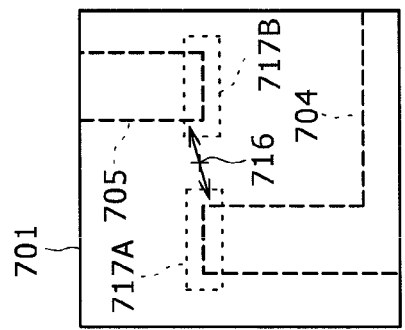
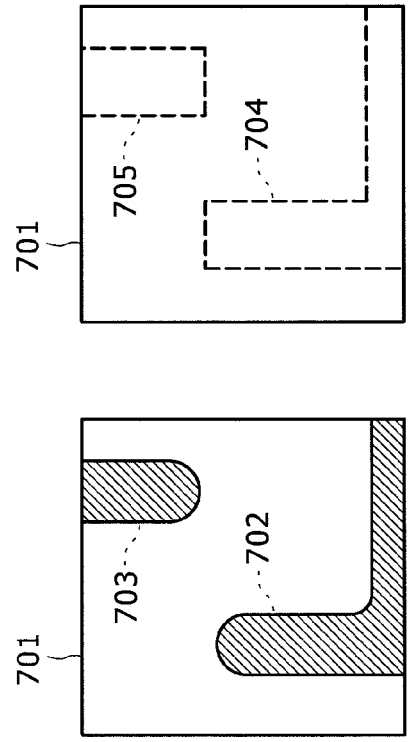
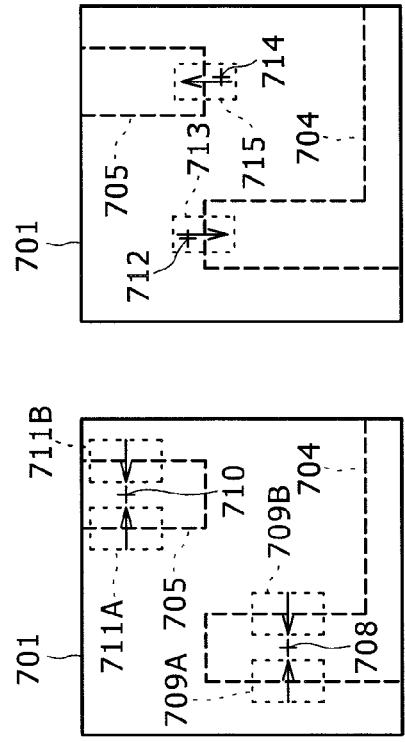

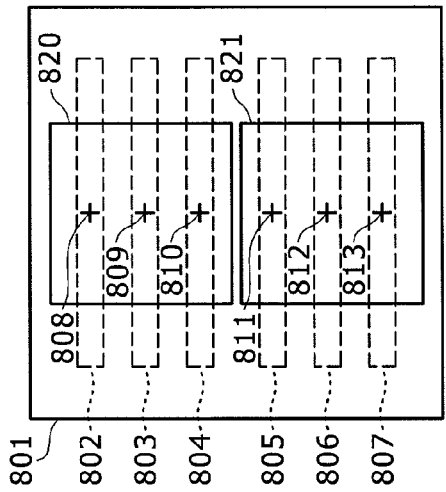
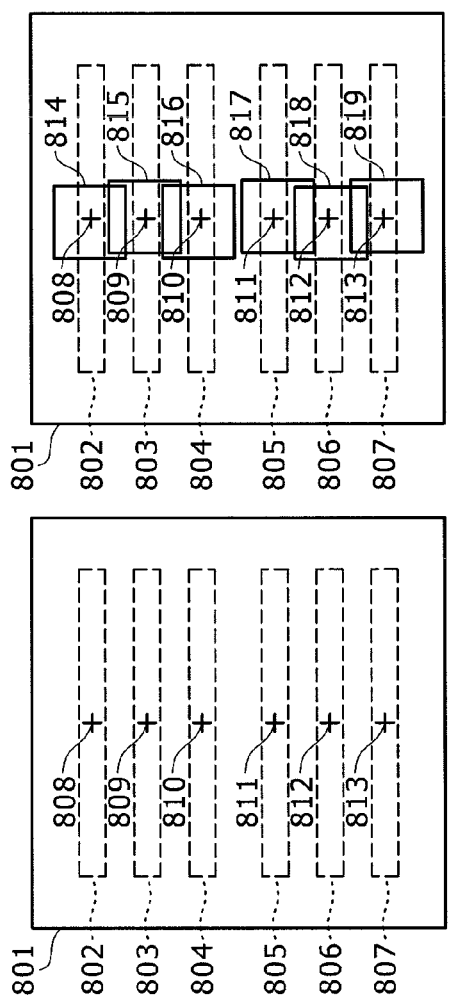
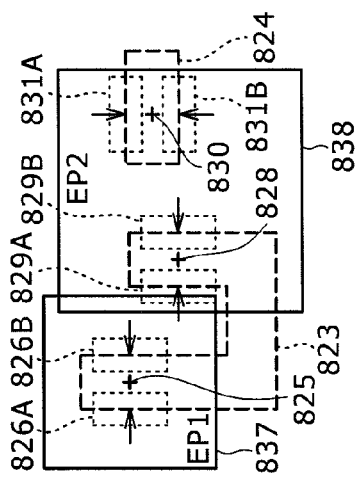
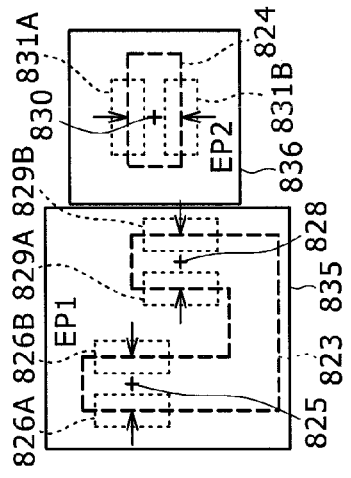
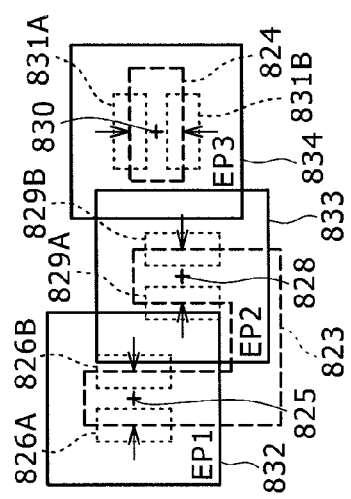

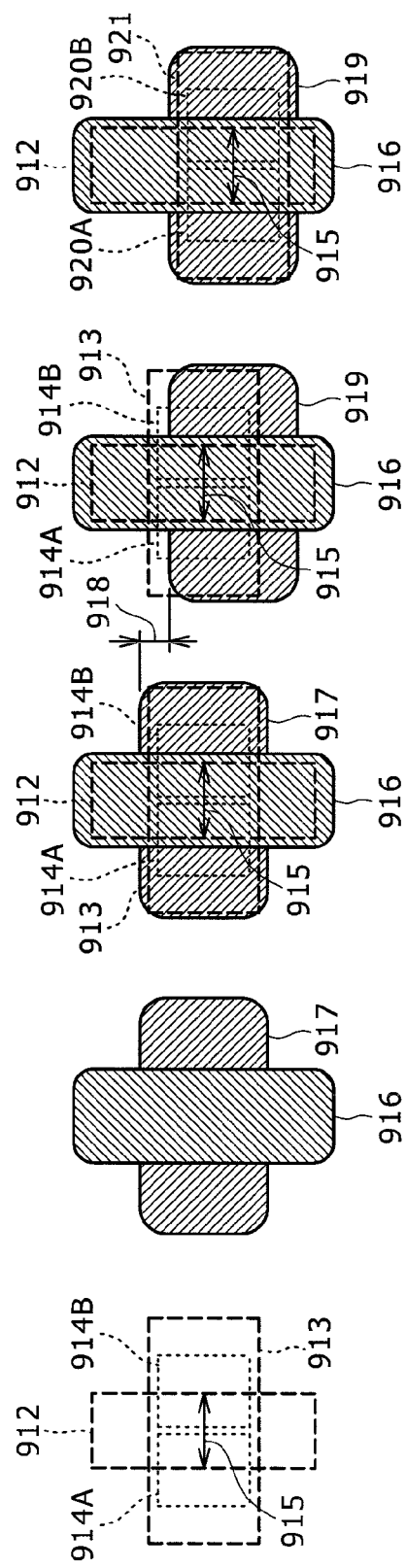

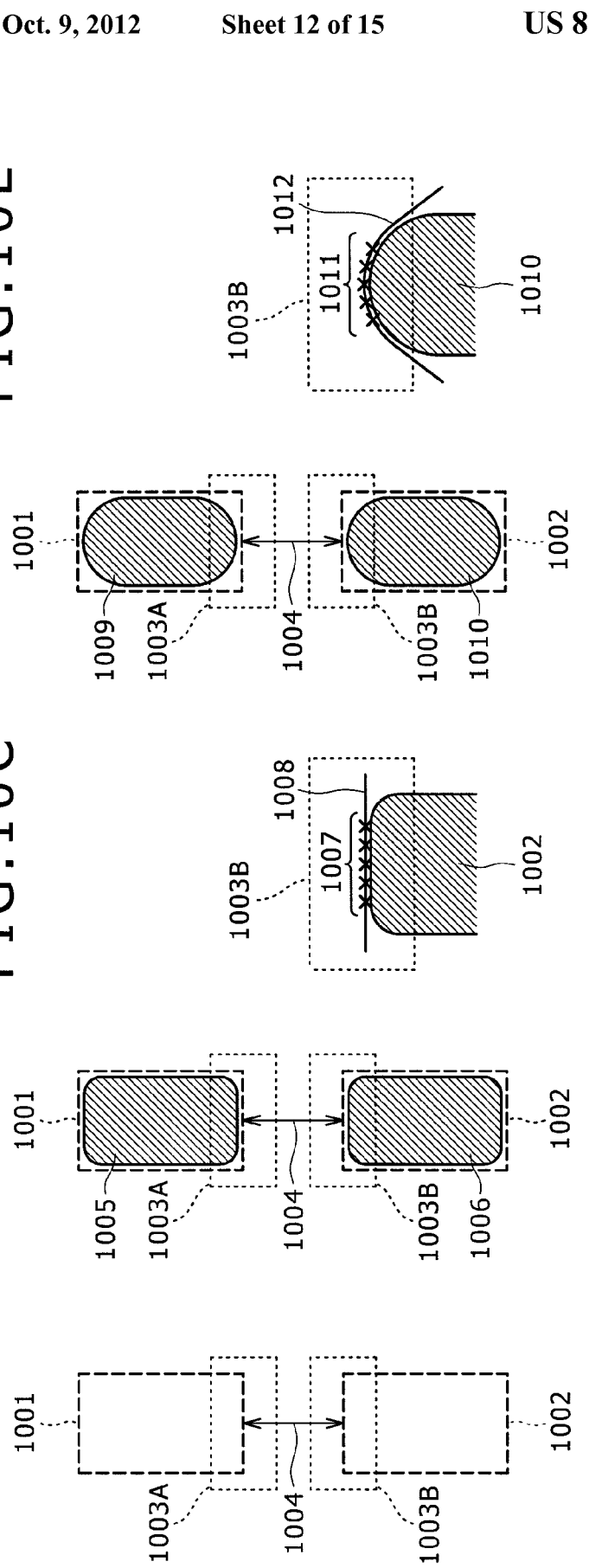

FIG.11A
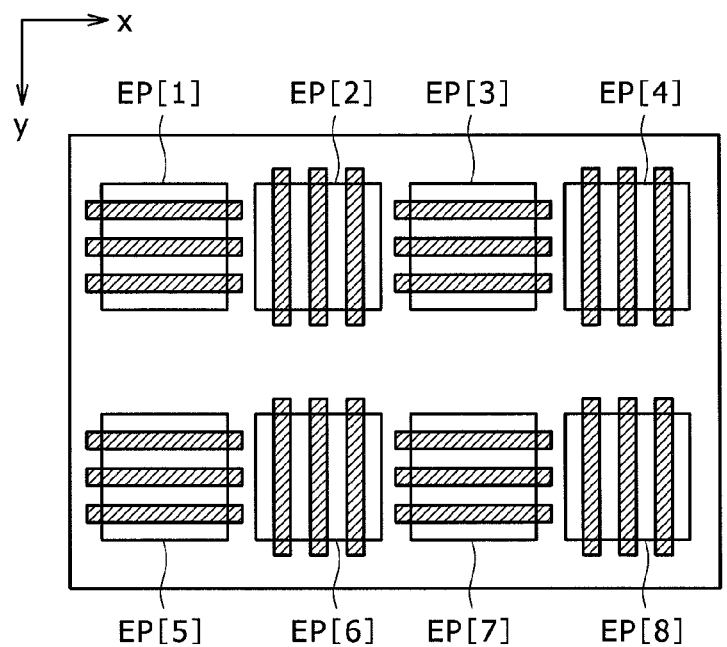
FIG.11B  FIG.11C  FIG.11D  FIG.11E
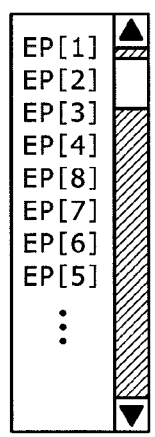 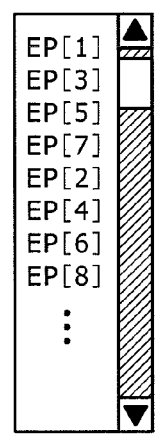 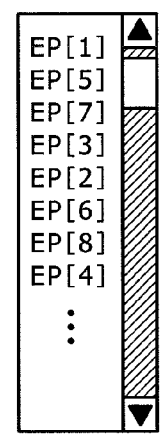 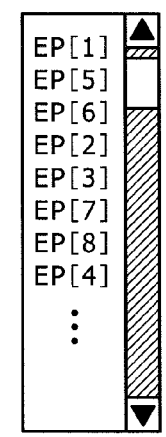

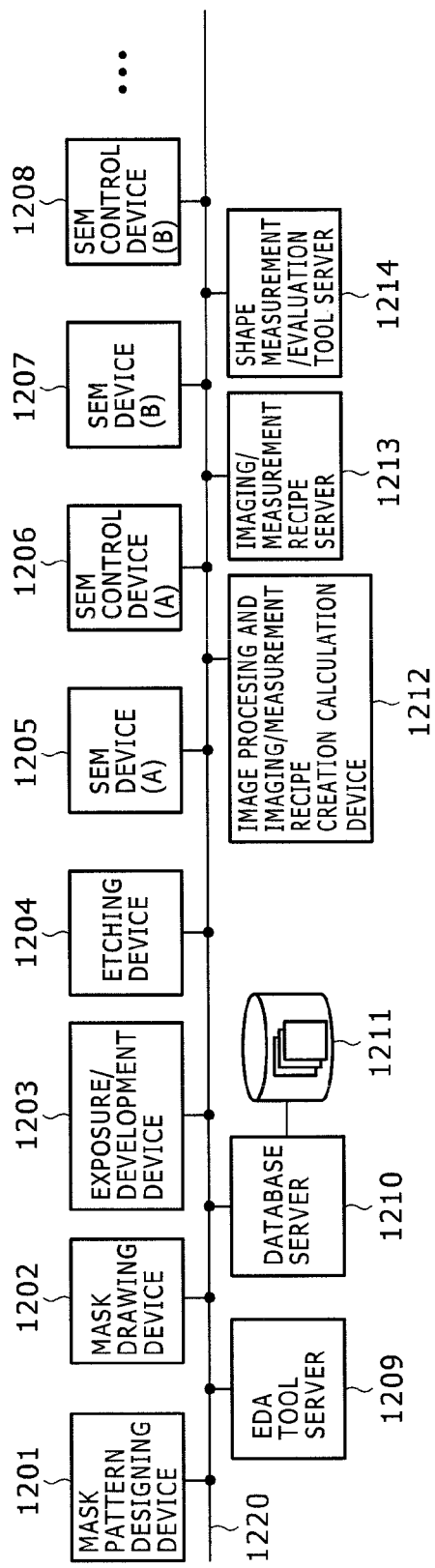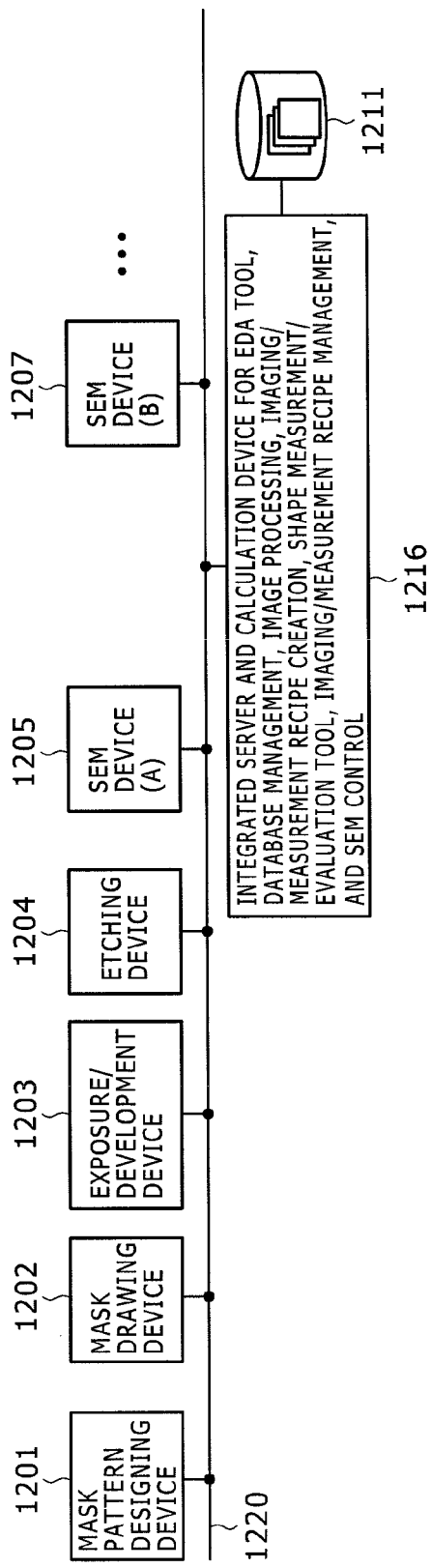

METHOD AND APPARATUS FOR MEASURING DIMENSION OF CIRCUIT PATTERN FORMED ON SUBSTRATE BY USING SCANNING ELECTRON MICROSCOPE

CROSS REFERENCE TO RELATED APPLICATION

This application is a continuation of U.S. application Ser. No. 12/354,923, filed Jan. 16, 2009 now U.S. Pat. No. 7,888,638, the contents of which are incorporated herein by reference.

BACKGROUND OF THE INVENTION

The present invention relates to a scanning electron microscope (SEM) capable of imaging a desired evaluation point on a sample and automatically measuring a desired dimension of a circuit pattern formed at the evaluation point, and to a measuring method therefor. Specifically, the present invention relates to an SEM device provided with an automatic recipe creating function of obtaining an SEM image of the desired evaluation point and automatically determining a recipe making it possible to perform a desired measurement (e.g., a measurement of wiring width of the line pattern or a measurement of a gap between the line patterns) at the evaluation point based on the design data of the circuit pattern without using a real wafer, and to a measuring method therefor. In the recipe, there are designated an imaging method of the SEM image of the evaluation point, a position and a shape of a dimension measurement cursor for measuring the dimension in the desired circuit pattern after taking the SEM image, and a dimension measurement method.

When forming a wiring pattern on a semiconductor wafer, there is adopted a method in which a coating material called resist is applied on the semiconductor wafer, an exposure mask (a reticle) for the wiring pattern is stacked on the resist, a visible light beam, an ultraviolet ray, or an electron beam is applied on the exposure mask, thereby exposing the resist to be developed, thus forming the wiring pattern with the resist on the semiconductor wafer, and then an etching treatment is executed on the semiconductor wafer using the wiring pattern, which is made of the resist, as a mask, thereby forming the wiring pattern. Since the wiring pattern made of the resist varies in the form of the pattern depending on the intensity and aperture of the visible light beam, the ultraviolet ray, of the electron beam applied to the wiring pattern, it is necessary to examine the facture of the pattern in order to form a highly accurate wiring pattern. In the examination described above, critical dimension scanning electron microscopes (CD-SEM) have been used widely in the past.

The coordinate point, at which the SEM imaging is performed for evaluating the pattern shape, is called an evaluation point, and hereinafter abbreviated as EP. The EP is designated by the user in some cases, or provided by the coordinates of a hot spot (a critical point) on the semiconductor pattern to be examined in other cases. The coordinates of the hot spot can be estimated by an exposure simulation or the like. Various dimensional values such as the wiring width of the pattern are measured based on the SEM image, and the facture of the pattern is evaluated based on these dimensional values. The result of the evaluation is fed-back to a shape correction of the mask pattern and semiconductor manufacturing process conditions, thus a high yield is realized.

In order to take an image of the EP with a small amount of imaging position misalignment and a high image quality, the following process is executed prior to the imaging of the EP. Firstly, some or all of adjustment points such as an addressing point (hereinafter referred to as AP), an automatic focus adjustment point (hereinafter referred to as AF), an automatic astigmatism adjustment point (hereinafter referred to as AST), or an automatic brightness/contrast adjustment point (hereinafter referred to as ABCC) are set if necessary. Then, addressing, an automatic focus adjustment, an automatic astigmatism adjustment, or an automatic brightness/contrast adjustment is executed at the respective adjustment points. The amount of imaging position misalignment in the addressing described above is corrected using an amount of matching difference as the amount of position misalignment of imaging. The amount of matching is obtained by matching an SEM image at the AP with known coordinates previously registered as a registered template and an SEM image (a real imaging template) observed in the actual imaging sequence with each other. The evaluation point (EP) and the adjustment points (AP, AF, AST, and ABCC) are collectively called imaging points. A position and imaging conditions of EP, and an imaging sequence and imaging conditions, an adjustment method, and the registered template of each of an imaging sequence for taking an image of the EP are managed as an imaging recipe, and the SEM executes imaging of the EP based on the imaging recipe.

When the SEM image at the EP is obtained, a desired dimension of the semiconductor pattern at a measurement point (hereinafter referred to as MP) to be measured in the EP using the SEM image.

Conventionally, the operator of the SEM manually create the recipe, and the creation of the recipe is an operation requiring energy and time. Further, since in order to register the determination of each of the adjustment points and the registered templates in the recipe, it is required to actually take an image of the wafer at low magnification, the creation of the recipe is a factor of lowering the operation rate of the SEM device. Further, as the pattern becomes miniaturized and complicated, the number of EP required to be evaluated increases explosively, and it is getting unrealistic to create the recipe manually from viewpoints of energy and creation time.

Therefore, regarding the imaging recipe, there is disclosed, in JP-A-2002-328015, a semiconductor inspection system for determining the AP based on the design data of the circuit pattern of the semiconductor described in, for example, GDSII format, further clipping the data in the AP out of the design data, and registering the data in the AP to the imaging recipe as the registered template. In this dace, since there is no need for taking an image of a real wafer only for the purpose of determination of the AP and registration of the registered template, improvement of operation rate of the SEM can be achieved. Further, the system has a function of matching, when the SEM image (a real image template) at the AP has been obtained in the actual imaging sequence, the real image template and the registered template in the design data with each other, re-registering the SEM image corresponding to the position of the registered template of the design data to the imaging recipe as the registered template, and thereafter using the registered template of the SEM image thus re-registered in the addressing processing. Further, the system has a function of automatically detecting a characteristic part of the pattern from the design data, and registering the part as the AP.

Further, JP-A-2007-250528 describes a method of creating the imaging recipe for observing the EP using CAD data. The document describes that some or all of the items including the number, coordinates, and dimensions/shapes of imaging points, an imaging sequence, a method of changing an imaging position, and imaging conditions necessary for the observation are automatically obtained from the CAD data. The document further describes that an operation of creating the image recipe is executed offline using the CAD data instead of the SEM image of a real wafer.

In other words, in the related art, the specification and the characteristics of the measurement tool (SEM) side for realizing the measurement expected by the user at the EP has not been considered. Therefore, there have arisen many cases in which correction of the recipe by the operator is required after the recipe has been created.

Further, in the related art, there has been made no consideration of sharing the recipe creation system and the information created or obtained by the system among a plurality of SEM devices, and therefore, recipe creation is required to be executed by every device. Further, there has been made no consideration of sharing the imaging/measurement data obtained from a plurality of devices.

SUMMARY OF THE INVENTION

The present invention relates to an SEM device provided with an automatic creation function for the imaging/measurement recipe and a method therefor, and is in particular for providing a recipe creation method expected to solve the following problems arising in the automatic creation of the measurement recipe thereby reducing the correction of the recipe by the operator, and improving the accuracy of imaging or measurement compared to the related art.

Specifically, according to the present invention, it becomes possible to create the recipe of the SEM in a waferless and offline (without using the SEM device) condition, and in an automatic manner by using the design data.

Further, in the recipe creation procedure, it is arranged to make consideration not only of the viewpoint of simply taking an image of the EP designated by the user, but also of the specification and the characteristics of the measurement tool (SEM) side for realizing the measurement expected by the user at the EP.

Further, it is arranged that the recipe creation system and the information created or obtained by the system are shared among a plurality of SEM devices.

Specifically, in order to solve the problems described above, in the present invention, a method of measuring a dimension of a circuit pattern formed on a substrate using a scanning electron microscope, includes the steps of (a) inputting a position information of a circuit pattern having a dimension to be measured out of the circuit pattern formed on the substrate, and design information of the circuit pattern including the circuit pattern having the dimension to be measured, and formed on the substrate, (b) setting a measurement object area including an edge of the circuit pattern having the dimension to be measured using the position information of the circuit pattern having the dimension to be measured and the design information, and an imaging area and an imaging condition for imaging an area including the measurement object area thus set with a scanning electron microscope, (c) setting an imaging sequence for imaging the imaging area with the scanning electron microscope for measuring the dimension of the circuit pattern, (d) imaging the circuit pattern formed on the substrate with the scanning electron microscope based on the imaging condition and the imaging sequence, and (e) processing the image obtained by imaging to measure the dimension of the circuit pattern, wherein step (b) includes the steps of setting, as an area including a position at which the dimension of the circuit pattern is measured, an area including the edge of the circuit pattern in the vicinity of the position at which the dimension of the circuit pattern is measured, and setting in accordance with a direction of the edge of the circuit pattern included in the area, a direction of continuous scanning of an electron beam scanned in the scanning electron microscope.

Further, in order to solve the problems described above, in the present invention, a method of measuring a dimension of a circuit pattern formed on a substrate using a scanning electron microscope, includes the steps of (a) inputting a position information of a circuit pattern having a dimension to be measured out of the circuit pattern formed on the substrate, and design information of the circuit pattern including the circuit pattern having the dimension to be measured, and formed on the substrate, (b) setting a measurement object area including an edge of the circuit pattern having the dimension to be measured using the position information of the circuit pattern having the dimension to be measured and the design information, and an imaging area and an imaging condition for imaging an area including the measurement object area thus set with a scanning electron microscope, (c) imaging the circuit pattern formed on the substrate with the scanning electron microscope based on the imaging condition, and (d) processing the image obtained by imaging to measure the dimension of the circuit pattern using information of the edge of the circuit pattern having the dimension to be measured included in the imaging area, wherein step (b) includes the steps of setting a type of the dimension to be measured using the position information of the circuit pattern having the dimension to be measured and the design information, and setting the measurement object area in accordance with the type of the dimension to be measured.

Further, in order to solve the problems described above, in the present invention, an apparatus adapted to measure a dimension of a circuit pattern formed on a substrate using a scanning electron microscope, includes input means for inputting a position information of a circuit pattern having a dimension to be measured out of the circuit pattern formed on the substrate, and design information of the circuit pattern including the circuit pattern having the dimension to be measured, and formed on the substrate, imaging condition setting means including a measurement object area setting section adapted to set a measurement object area including an edge of the circuit pattern having the dimension to be measured using the position information of the circuit pattern having the dimension to be measured and the design information, and an area/condition setting section adapted to set an imaging area and an imaging condition for imaging an area including the measurement object area thus set by the measurement object area setting section with a scanning electron microscope, imaging sequence setting means for setting an imaging sequence for imaging the imaging area, which is set by the imaging condition setting means for measuring the dimension of the circuit pattern, with the scanning electron microscope, scanning electron microscope means for imaging the circuit pattern formed on the substrate based on the imaging condition set by the imaging condition setting means and the imaging sequence set by the imaging sequence setting means, and image processing means for processing the image obtained by imaging with the scanning electron microscope means to measure the dimension of the circuit pattern, wherein the measurement object area setting section of the imaging condition setting means sets, as an area including a position at which the dimension of the circuit pattern is measured, an area including the edge of the circuit pattern in the vicinity of the position at which the dimension of the circuit pattern is measured, and the imaging condition means further includes a scanning direction setting section adapted to set a direction of continuous scanning of an electron beam scanned in the scanning electron microscope in accordance with a direction of the edge of the circuit pattern included in the area set by the measurement object area setting section.

Further, in order to solve the problems described above, in the present invention, an apparatus adapted to measure a dimension of a circuit pattern formed on a substrate using a scanning electron microscope, includes input means for inputting a position information of a circuit pattern having a dimension to be measured out of the circuit pattern formed on the substrate, and design information of the circuit pattern including the circuit pattern having the dimension to be measured, and formed on the substrate, imaging condition setting means including a measurement object area setting section adapted to set a measurement object area including an edge of the circuit pattern having the dimension to be measured using the position information of the circuit pattern having the dimension to be measured and the design information input by the input means, and an area/condition setting section adapted to set an imaging area and an imaging condition for imaging an area including the measurement object area thus set by the measurement object area setting section with a scanning electron microscope, scanning electron microscope means for imaging the circuit pattern formed on the substrate, based on the imaging condition set by the imaging condition setting means, and image processing means for processing the image obtained by imaging with the scanning electron microscope means to measure the dimension of the circuit pattern using information of the edge of the circuit pattern having the dimension to be measured included in the imaging area, wherein the imaging condition setting means further includes a dimension measurement type setting section adapted to set a type of the dimension to be measured using position information of the circuit pattern having the dimension to be measured and the design information input by the input means, and the imaging condition setting means sets the area including the edge of the circuit pattern as the measurement object area in accordance with the type of the dimension to be measured set by the dimension measurement type setting section in the measurement object area setting section.

In the present invention, when the SEM image at the EP is obtained, a desired dimension of the semiconductor pattern at a measurement point (hereinafter referred to as MP) to be measured in the EP using the SEM image. As the desired dimension, a line width of the line pattern, an amount of gap between the line patterns, and so on can be cited, and hereinafter such variations of measurement in the MPs are called dimension measurement types. In some cases, a plurality of MPs exists in the EP. Then, an example of a measurement method will be explained exemplifying the measurement of a line width (a distance between the right and left edges of a line) of a line pattern as the dimension measurement type. In order to measure the line width correctly, it is required to accurately and stably measure the positions of the right and left edges of the line. Therefore, there is a method in which an area with a predetermined dimension including the edge is set on each of the right and the left edges, and a cumulative profile less subject to the image noise or the line edge roughness is obtained by accumulating the SEM signal in the area in the line direction, and the edge position is detected using the profile. The measurement object area (the area on the SEM image referred to by obtaining the measured value) with a predetermined dimension including the edge is designated by a box called a dimension measurement cursor. The position and the shape of the dimension measurement cursor, a dimension measurement method (a dimension measurement algorithm and a dimension measurement parameter) are managed as a measurement recipe, and the SEM performs the measurement at the EP based on the measurement recipe.

In the present specification, the terms an imaging recipe and a measurement recipe are used along the definitions described above. It should be noted that the definitions of the imaging recipe and the measurement recipe are nothing more than an example, the setting items designated by the respective recipes can be managed in arbitrary combinations. Therefore, in the case in which the imaging recipe and the measurement recipe are not particularly discriminated, both recipes are collectively called simply a recipe or an imaging/measurement recipe.

According to the present invention, it becomes possible for everyone to automatically and quickly create the highly accurate recipe in the waferless condition and without an extraordinary knowledge about the SEM. The advantages of the present invention can be summarized as the following items (1) through (3).

(1) By using the design data, it becomes possible to automatically create the recipe of the SEM in a waferless, offline (without using the SEM device) condition, which leads to reduction of burden of the operator and improvement of the operation rate of the SEM device. Further, the automation of the operation allows the recipe creation independent of difference in skill between the operators.

(2) In the recipe creation procedure according to the present invention, since the specification and characteristic of the measurement tool (SEM) for realizing the measurement intended by the user at the EP are also taken into consideration, in addition to the viewpoint of simply imaging the EPs designated by the user, it can be expected to reduce the frequency of the case in which the recipe correction by the operator becomes necessary after the recipe has once been created, and to improve the strictness of the imaging or the measurement compared to the related art.

(3) By sharing the recipe creation system and the information created or obtained by the system among a plurality of SEM devices, it can be eliminated to execute the recipe creation by every device. Further, since the result data including successful cases and failed cases in the imaging/measurement obtained from a plurality of devices can be shared, it is possible to collect a lot of result data quickly, and if a problem exists in the recipe creation rule, for example, a measure against the problem can quickly be taken based on the result data.

These and other objects, features and advantages of the invention will be apparent from the following more particular description of preferred embodiments of the invention, as illustrated in the accompanying drawings.

2B is a diagram showing a method of imaging the amount of signal obtained by detecting electrons emitted from the surface of the semiconductor wafer.

Figure 3A:
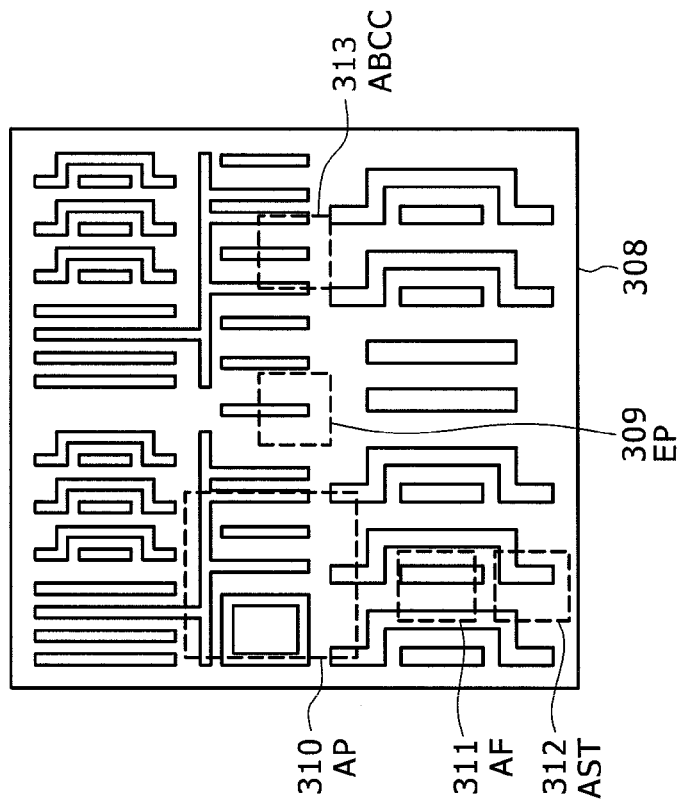
Figure 3B:
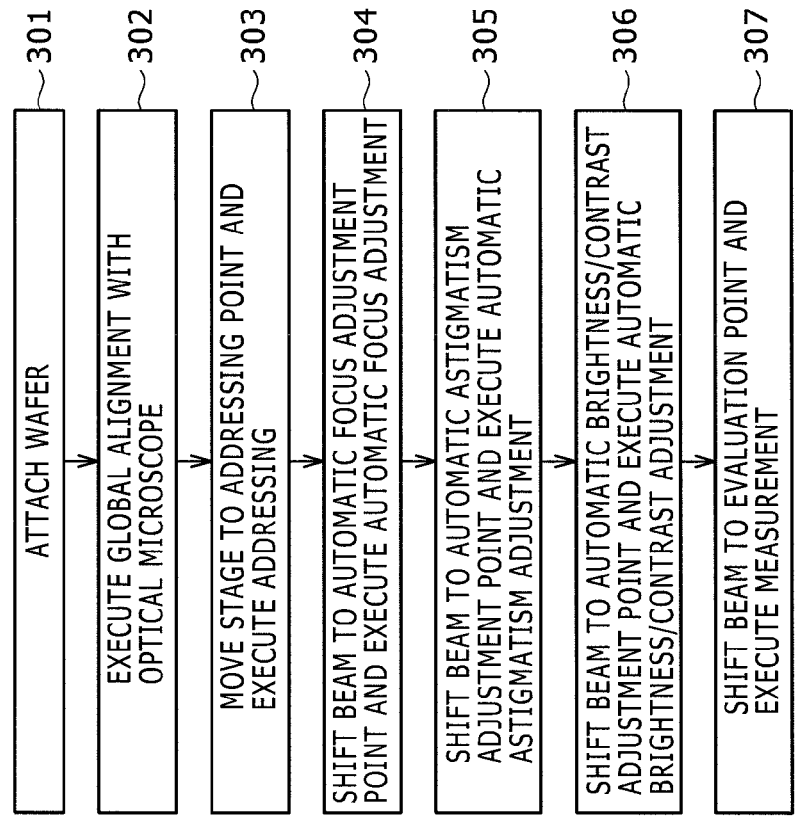

FIG. 3A is a flowchart representing an imaging sequence, and FIG. 3B is a diagram showing positions corresponding to respective imaging steps of the flowchart in a beam shift allowable area from evaluation points (EP).

Figure 4:
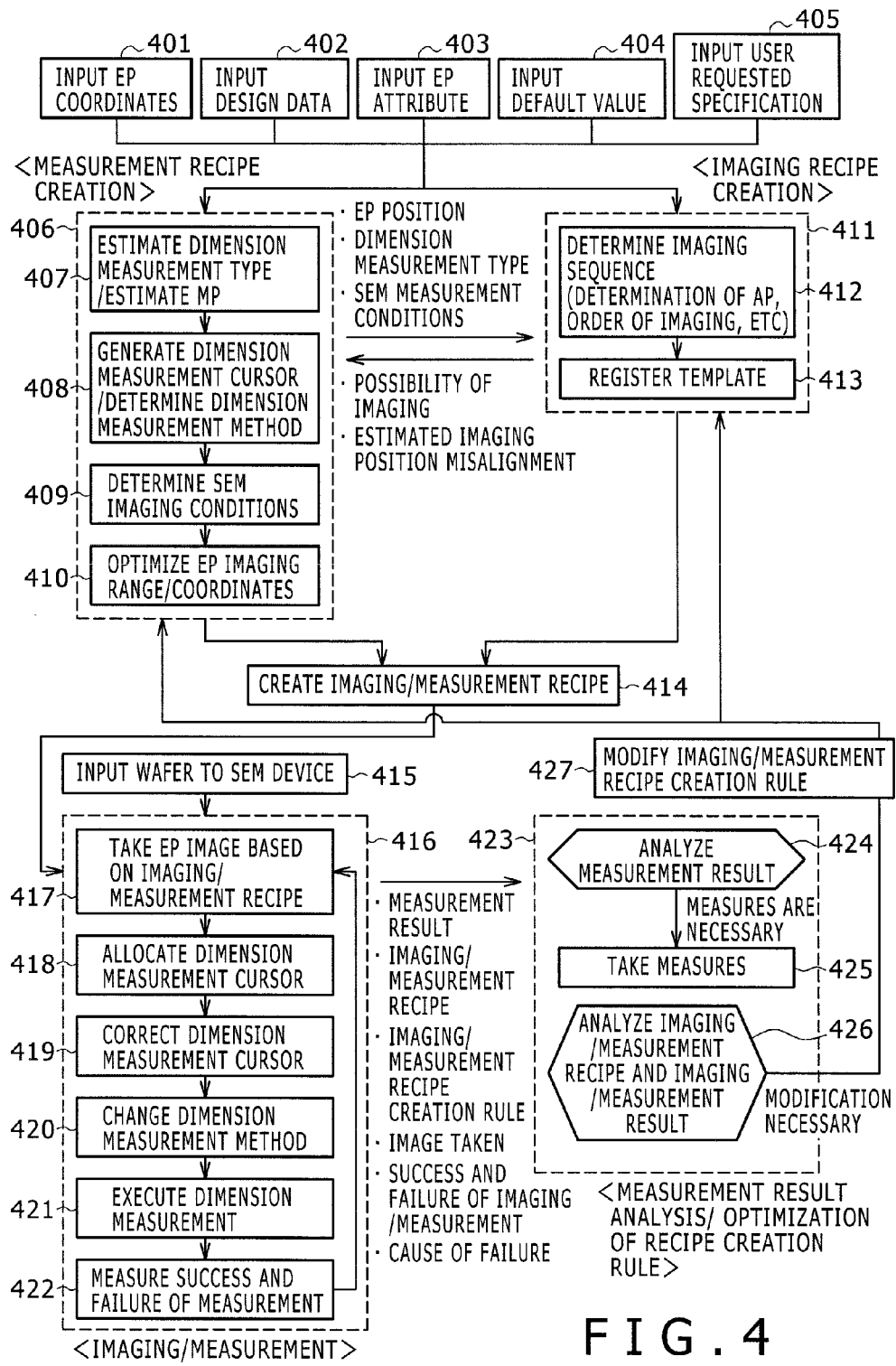

FIG. 4 is a chart for showing an overall processing flow for creating the recipe.

Figure 5:
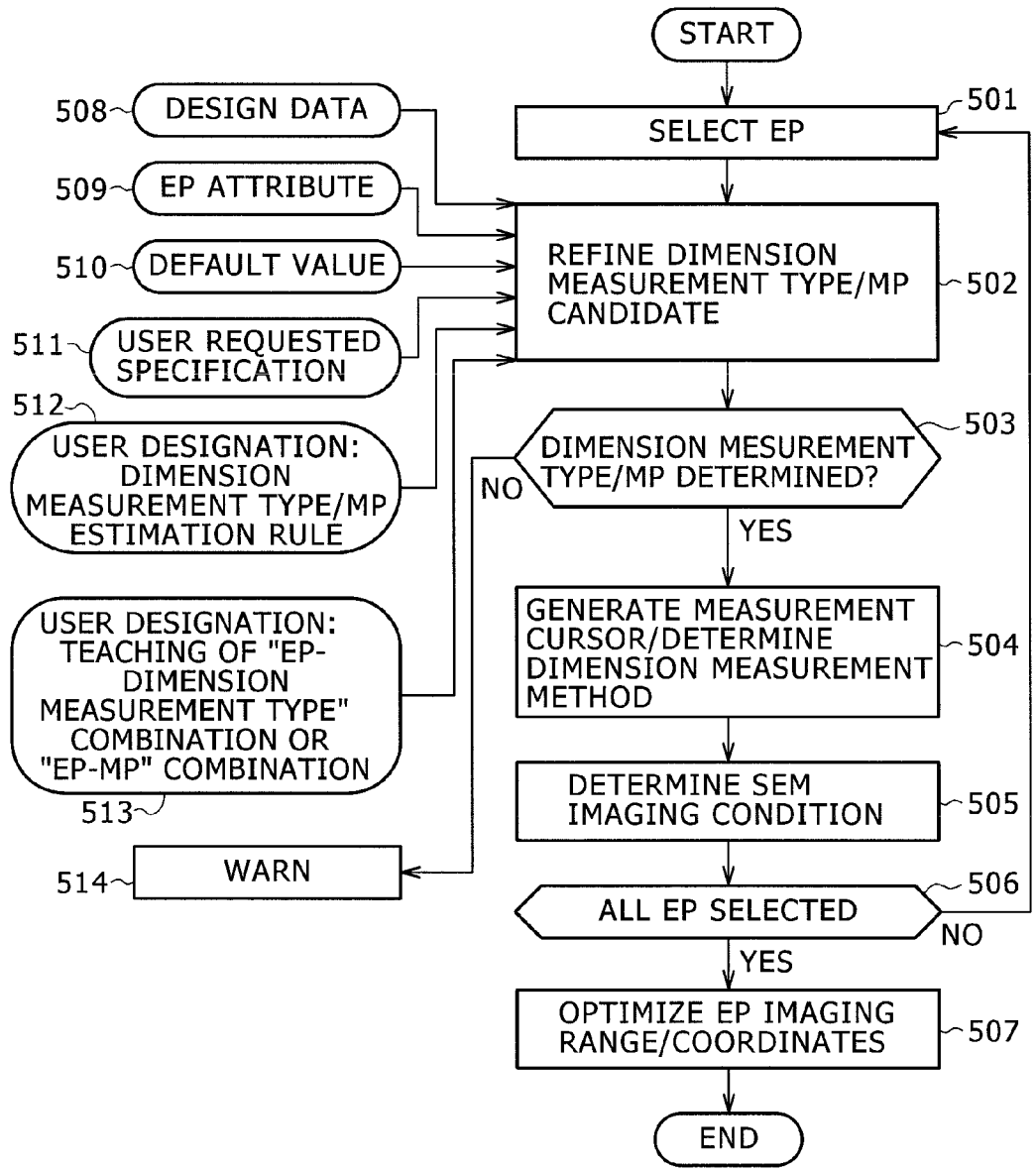

FIG. 5 is a chart showing an estimation flow for a dimension measurement type/measurement point in the evaluation point.

Figure 6A:
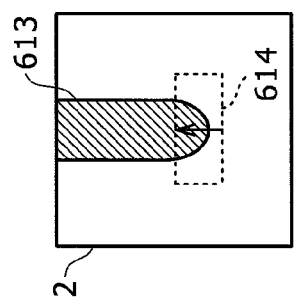
Figure 6B:
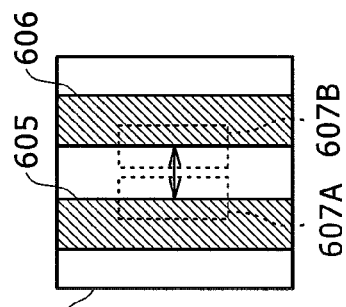
Figure 6C:
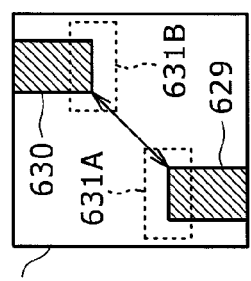
Figure 6E:
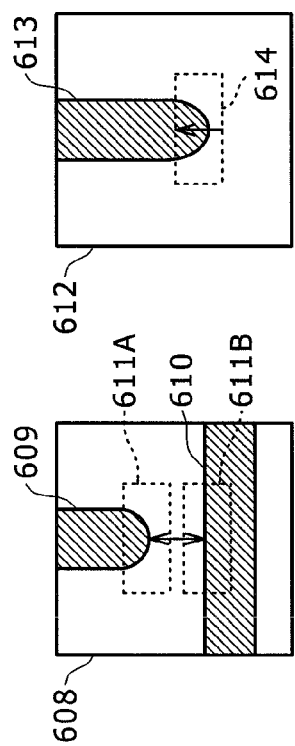
Figure 6F:
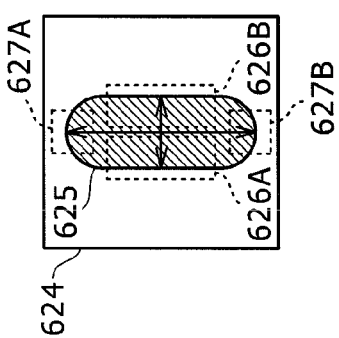
Figure 6G:
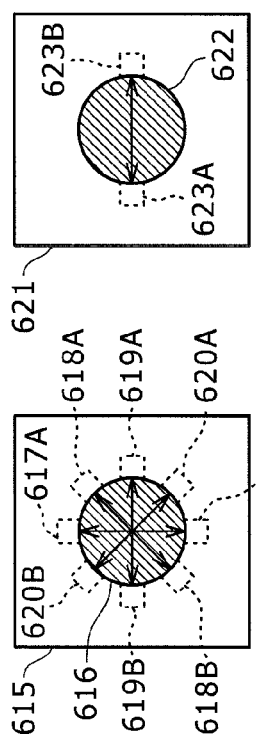
Figure 6H:
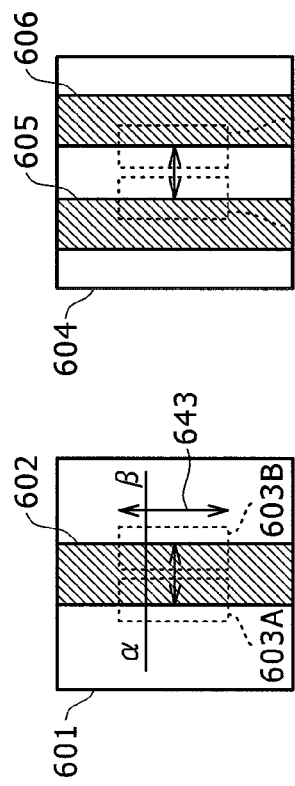

FIG. 6A is a diagram showing an example of the case in which the dimension measurement type is a line width of a line pattern, FIG. 6B is a diagram showing an example of the case in which the dimension measurement type is a distance between the line patterns, FIG. 6C is a diagram showing an example of the case in which the dimension measurement type is a gap between a line end section of the line pattern and the line pattern, FIG. 6D is a diagram showing an example of the case in which the dimension measurement type is an amount of recession of the end section of the line pattern, FIG. 6E is a diagram showing an example of the case in which the dimension measurement type is a diameter of a contact hole and the diameter is measured in tow or more directions, FIG. 6F is a diagram showing an example of the case in which the dimension measurement type is a diameter of a contact hole and the diameter is measured in one direction, FIG. 6G is a diagram showing an example of the case in which the dimension measurement type is dimensions of a major axis and a minor axis of the line pattern, FIG. 6H is a diagram showing an example of the case in which the dimension measurement type is a gap width between the line patterns, FIG. 6I is a diagram showing an example of the case in which the dimension measurement type is a shape of the pattern, FIG. 6J is a diagram enlargedly showing a part of FIG. 6I, FIG. 6K is a diagram showing an SEM signal profile corresponding to the line between α and β shown in FIG. 6A, FIG. 6L is an enlarged diagram of FIG. 6A, FIG. 6M is a diagram showing an example of the case in which the dimension measurement type is a line width of the line pattern extending in the y direction, FIG. 6N is a diagram showing an example of the case in which the dimension measurement type is a line width of the line pattern extending in the x direction, FIG. 6O is a diagram showing an example of the case in which the dimension measurement type is a line width of the line pattern extending in the x direction and there is a view field misalignment in the x direction, and FIG. 6P is a diagram showing an example of the case in which the dimension measurement type is a gap between the line patterns, and a part of a dimension measurement cursor runs out of the view field due to the view field misalignment.

FIG. 7A is a diagram showing an example of two patterns included in the view field of the evaluation point (EP), FIG. 7B is a diagram showing the design data corresponding to the EP shown in FIG. 7A, FIG. 7C is a diagram showing a pattern obtained by modifying the pattern as designed, FIG. 7D is a diagram showing an example of measurement points of the line patterns in the x direction estimated from the design data, FIG. 7E is a diagram showing an example of measurement points of the end sections of line patterns in the y direction estimated from the design data, FIG. 7F is a diagram showing an example of measurement points of a gap between the line patterns estimated from the design data, and FIG. 7G is a diagram showing an example of OPC shape measurement points estimated from the design data.

FIG. 8A is a diagram showing the case in which the line width of each of the six line patterns is measured, FIG. 8B is a diagram showing the condition in which the measurement points of the six line patterns are set so as to be included in the view fields of the EPs, FIG. 8C is a diagram showing the condition in which the EPs are set to be optimized so that the imaging ranges do not overlap with each other, FIG. 8D is a diagram showing the condition in which there exist three measurement points in the design data and the EP is set corresponding to each of the measurement points, FIG. 8E is a diagram showing the condition in which two EPs out of the three EPs corresponding respectively to the three measurement points are merged with each other, and FIG. 8F is a diagram showing the condition in which two EPs, a different combination thereof from the combination shown in FIG. 8E, out of the three EPs corresponding respectively to the three measurement points are merged with each other.

Figure 9A:
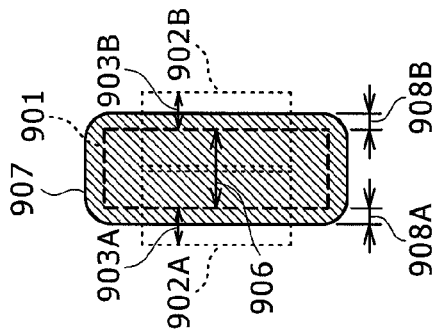
Figures 9B, 9C, 9D:
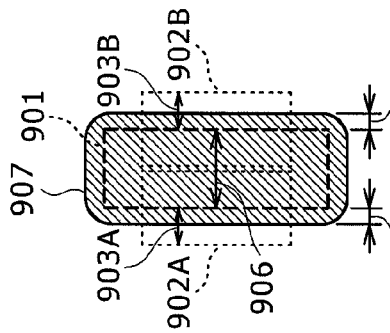
Figure 9E:
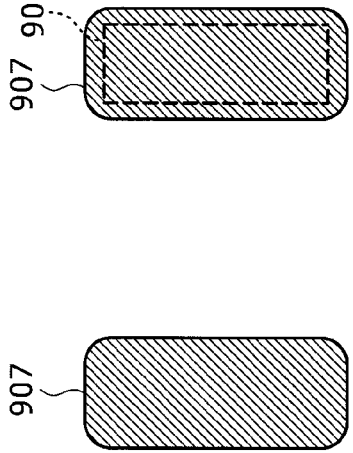
Figure 9F:
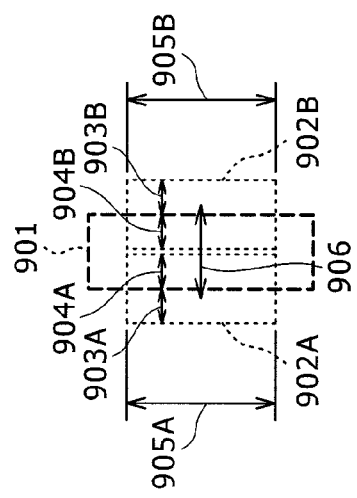

FIG. 9A is a diagram showing the condition in which the dimension measurement cursors are disposed on the design data, FIG. 9B is a diagram showing the line pattern observed by an SEM device, FIG. 9C is a diagram showing the condition in which the design data is matched with the SEM image of the pattern, FIG. 9D is a diagram showing the condition in which the dimension measurement cursors are displayed so as to overlap on the SEM image, FIG. 9E is a diagram showing the condition in which the positions of the dimension measurement cursors are shifted in accordance with the edge positions of the pattern on the SEM image, FIG. 9F is a diagram showing an example in which a correction has been made so as to extend the profile reference range outside the line pattern in the case in which the skirt sections of the white band protrusions are long in the SEM signal profile of the line pattern, FIG. 9G is a diagram showing the design data of an upper layer pattern and a lower layer pattern, FIG. 9H is a diagram showing the patterns on the SEM image corresponding to the patterns on the design data shown in FIG. 9G, FIG. 9I is a diagram showing the condition in which the patterns on the design data and the patterns on the SEM image are matched with each other, and the dimension measurement cursors are disposed thereon, FIG. 9J is an SEM image in the condition in which the upper layer pattern and the lower layer pattern are misaligned to each other due to a fault in the manufacturing process, and FIG. 9K is a diagram showing the condition in which the patterns on the design data is matched with the SEM image in the condition in which the upper layer pattern and the lower layer pattern are shifted from each other, and the dimension measurement cursors are disposed thereon.

FIG. 10A is a diagram showing two patterns on the design data and a pair of cursors for measuring the distance between the two patterns, FIG. 10B is a diagram showing a matching result of the pattern of the SEM image and the pattern as designed, FIG. 10C is an enlarged view of a part of the dimension measurement cursor shown in FIG. 10B, FIG. 10D is an SEM image of the patterns with corners rounded due to the resolution limit of the lithography, and FIG. 10E is an enlarged view of a part of the dimension measurement cursor shown in FIG. 10D.

FIG. 11A is a diagram showing the condition in which eight EPs exist in a low magnification image area of the SEM, FIG. 11B is a part of a GUI showing an initial imaging order, FIG. 11C is a part of the GUI showing the imaging order with the reduced number of times of rotation compared to the imaging order shown in FIG. 11B, FIG. 11D is a part of the GUI showing the imaging order with the reduced total distance of view field movement between the EPs compared to the imaging order shown in FIG. 11B, and FIG. 11E is a part of the GUI showing the imaging order determined in consideration of the time required for a rotation and the time required for the view field movement between the EPs in the case in which the time required for a rotation and the time required for the view field movement between the EPs are roughly the same.

FIG. 12A is a diagram showing a configuration of an apparatus system for realizing the present invention, and FIG. 12B is a diagram showing a configuration with some of the constituents of the system shown in FIG. 12A are integrated with each other.

Figure 13:
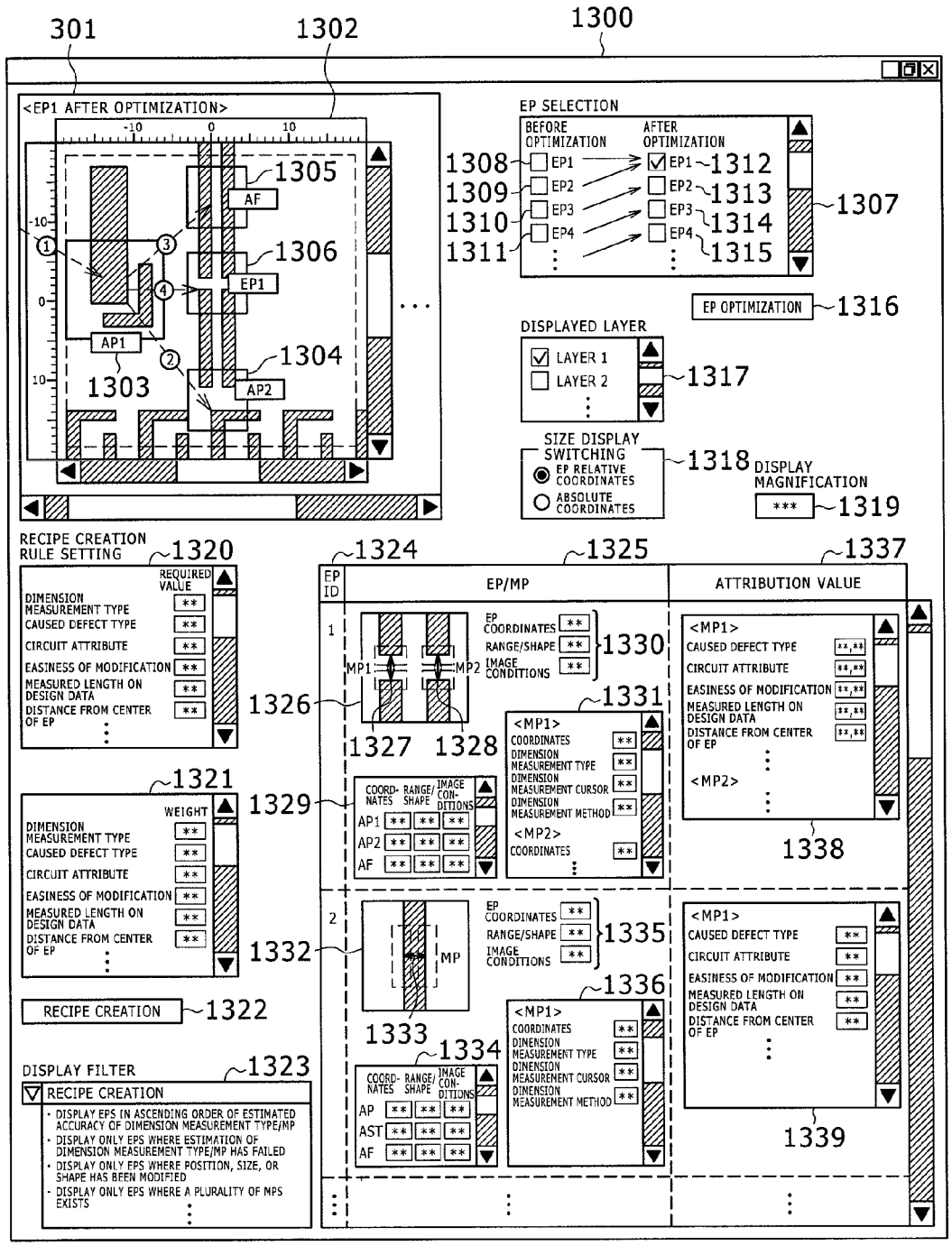

FIG. 13 is a diagram showing an example of the GUI screen according to the present embodiment.

DESCRIPTION OF THE PREFERRED EMBODIMENTS

The present invention relates to an SEM device provided with a function of automatically creating the recipe with the following means, and executing automatic imaging/measurement using the recipe, and a method therefor.

(1) According to a feature of the present invention, coordinate data of EPs and design data of circuit patterns including the EPs are used as an input, creation of the dimension measurement cursor for measuring the patterns existing in the EPs and selection or setting of the dimension measurement method are performed automatically based on the EP coordinate data and the design data. The dimension measurement cursor and the dimension measurement method are stored as a recipe. By performing the processing based on the resign data, there is no need for taking an SEM image when creating the recipe, and therefore, the operation can be carried out online, which leads to an improvement of the operation rate of the apparatus. As the coordinates of the EPs, there are input the coordinates of hot spots (critical points) detected based on the result of, for example, an exposure simulation executed by an EDA tool. Alternatively, in some cases, the coordinates of the EPs are input on a judgment of the user itself (taking the information of the EDA tool into consideration, if necessary).

In the creation of the dimension measurement cursor, the position and the shape of the dimension measurement cursor are determined on the design data (the dimension measurement cursor has the coordinates linking with the design data). Since the positional relationship between the design data and the SEM image can be obtained by actually taking the SEM image of the corresponding EP and matching the design data and the SEM image with each other, and the positional relationship between the dimension measurement cursor and the SEM image can also be obtained at the same time, the dimension measurement cursor can automatically be disposed on the SEM image.

Further, the selection or setting of the dimension measurement method specifically denotes the selection or setting of a dimension measurement algorithm or a dimension measurement parameter. The selection or setting described above is executed taking the information such as a dimension measurement type, or a shape or a direction of a pattern contour of the pattern to be measured into consideration if necessary.

(2) In the item (1) described above, in order to automatically create the dimension measurement cursor, it is necessary to know the coordinates of the measurement points (MP) to be measured in the EPs. Although there are some cases in which the EP coordinates (the center coordinates of the EP area) match with the MP coordinates, there are also the cases in which they do not match with each other, or the cases in which two or more MPs exist in the EP. Further, even if the MP coordinates are provided by the input from the user, there is a possibility that the coordinate values include an error. Therefore, according to another feature of the present invention, the MP coordinates are estimated inside the computer based on the coordinate data of the EPs and the design data of the circuit pattern including the EPs, and the dimension measurement cursor is created based on the MP coordinates thus estimated.

(3) In the item (1) described above, in order to automatically create the dimension measurement cursor, it is necessary to know the dimension measurement type of the MP in the EPs. In other words, the dimension measurement cursor can hardly be set without understanding what deformation of the pattern possibly occurs at the MP, and what dimensional value needs to be measured/controlled with respect to the deformation. Further, it is not easy for the user to manually designate all of such dimension measurement types. Therefore, according to another feature of the present invention, the dimension measurement types are estimated inside the computer based on the coordinate data of the EPs and the design data of the circuit pattern including the EPs, and the dimension measurement cursor is created based on the dimension measurement types thus estimated. Here, the dimension measurement types denote the variations of measurement at the MP, and as specific examples of the dimension measurement types, there are cited measurement of the line width of the line pattern, measurement of the gap between the line patterns, measurement of the amount of recession of the line end section, measurement of the diameter of the contact hole, measurement of the optical proximity correction (OPC) shape, and so on. Further, it is possible to include the information of a region to be measured such as the regions in the wiring area distance of which is measured in the dimension measurement type besides the category such as measurement of the line width. Further, it is also possible to include the information of a measurement direction such as a direction an amount of recession in which is measured in the measurement of "an amount of recession" in the dimension measurement type.

(4) According to another feature of the present invention, in the item (3) described above, a candidate (hereinafter, referred to as a candidate defect) of a possible defect in the EPs is provided, the dimension measurement type is estimated based on the information of the candidate defect, and the dimension measurement cursor is created based on the dimension measurement type thus estimated. The candidate defect denotes a defect mode in which the patterns can be linked with each other, or the pattern can be broken, for example. It is possible to input the candidate defect with the highest possibility of occurrence referring to the analysis result by, for example, EDA tool, or to input the candidate defect the user wants particularly to avoid. It is possible to input two or more candidate defects. How the SEM, the measurement tool, measures the MP (i.e., the dimension measurement type) is determined based on the information of the candidate defect so as to reflect the intension of the user on managing the shape of the pattern at the EP.

(5) According to another feature of the present invention, in the items (2) and (3) described above, in the estimation of the dimension measurement type/MP, at each of the pattern regions obtained from the circuit design pattern including the EPs, attribute information composed of at least one combination of a candidate of the dimension measurement type, a candidate of a possible defect, a circuit attribute, easiness of deformation, measurement dimension on the design data, and the distance from the center of the evaluation point is calculated, and the candidate of the dimension measurement type/MP at the EP is extracted along the estimation rule based on the attribute information. By taking a plurality of pieces of attribute information into consideration, the estimation of the dimension measurement type/MP with high accuracy becomes possible.

(6) In the item (5), in some cases, the creation of the estimation rule becomes a difficult operation for the user. Further, the default estimation rule prepared by the system can be different from the criteria of the user. Therefore, according to another feature of the present invention, as a mechanism for easily executing the user customization, the estimation rule is optimized in response to at least one combination teaching of EP and the position of the MP at the EP, or a combination teaching of the EP and the dimension measurement type at the EP.

(7) According to another feature of the present invention, in the item (1) described above, SEM imaging conditions at the EP are obtained based on the circuit design pattern including the EPs, and the conditions are stored in a recipe. According to another feature, the SEM imaging conditions include at least the scanning direction of the electron beam. Although the raster scan is common in the two-dimensional scanning of the electron beam for creating the SEM image, the obtained SEM image is different between, for example, the case in which the scanning of the two-dimensional area is performed by executing continuous electron beam scanning in the x direction a plurality of times while shifting the scanning position discretely in the y direction, and the case in which the scanning of the two-dimensional area is performed by executing continuous electron beam scanning in the y direction a plurality of times while shifting the scanning position discretely in the x direction. Therefore, it is effective to automatically setting the scanning method with which the SEM image advantageous to the measurement taking the measurement region and the measurement direction in the EP into consideration. The scanning method is not limited to the scanning in the direction parallel to the x or y direction, but can have variations such as scanning in an oblique direction or scanning in the direction varying in accordance with the position in the EP.

(8) According to another feature of the present invention, in the item (1) described above, the imaging range or the coordinates of the EP is optimized based on the information of the dimension measurement cursor. The imaging range should be determined from the viewpoint that the measurement of the desired region in the MP is realized with appropriate measurement accuracy in addition to the viewpoint of the range the user wants to check. Therefore, it is necessary to set the imaging range so as to include at least the range of the dimension measurement cursor required from the viewpoint of measurement accuracy. Further, it is possible to change the coordinates of the EP provided by the user if necessary. The optimization of the EP coordinates includes principally three items, (a) changing the coordinates of the EP and the imaging range, (b) merging a plurality of view fields of the EPs to newly set a single EP, and (c) dividing one EP to set a plurality of EPs, and any combinations of these items. Specific examples of the contents of the processing and the advantages of the respective cases will be described below.

In the case of (a), if the position of the MP (or the imaging area including the dimension measurement cursor necessary for measurement) is found, it becomes possible to determine whether or not the center of the EP is shifted from the MP, and if it is shifted, it becomes possible to take the image of the MP at roughly the center of the view field of the EP by matching the view field of the EP with the center of the MP. Further, for example, it is possible to adjust the imaging range so that the range of the dimension measurement cursor is sufficiently included in the view field of the EP with respect to the imaging misalignment.

In the case of (b), when imaging/measuring dense continuous patterns in sequence, for example, in some cases, the imaging ranges set respectively to the patterns overlap with each other. In this case, when taking an image of a certain EP, there is a possibility of causing contamination in the measurement area (the area of the SEM image necessary for performing measurement) included in another EP, thus degrading the measurement accuracy. Therefore, by resetting the EP area so that the patterns included in the respective EPs are collectively included in a single view field, the contamination in the measurement area described above can be prevented from occurring. When merging the EPs, the determination thereof can be made taking whether or not the dimension of the view field or the imaging magnification of the EP obtained by merging is within a predetermined dimension (since the measurement accuracy is generally lowered with the lower magnification) and whether or not the SEM imaging conditions (e.g., scanning direction of the electron beam) of the EPs to be merged match each other into consideration.

In the case of (c), if a plurality of MPs are included in the EP, and further, the directions of the patterns to be measured in the respective MPs are different from each other, and therefore, the SEM imaging conditions (e.g., the scanning direction of the electron beam) is required to be different between the MPs, it is effective to separate the MPs from each other as the EPs, thus taking images with the SEM imaging conditions different from each other. Further, in the case in which a number of MPs are included in the EP, and the MP is located closest to the edge of the view field of the EP, there is a possibility that a part of the measurement area of the MP runs off the view field due to the view field misalignment caused when taking the image of the EP. In such a case, division of the EP is effective.

(9) In the item (1) described above, it is required to set the order of taking the images of the EPs to the recipe when taking the images of a plurality of EPs. According to another feature of the present invention, the imaging order is optimized based on the coordinates of the EP and the SEM imaging conditions of the EP instead of directly taking the inputting order of the EPs by the user as the imaging order. In order to improve the throughput of the imaging in the EPs as a whole, it is effective to reduce the total moving distance of the stage shift and the image shift of the SEM. Further, it is also effective to decrease the number of times of the imaging condition changes taking the time necessary for changing the imaging conditions into consideration. Therefore, the imaging order with which the throughput is enhanced is determined based on the coordinates of the EPs and the EPs or the SEM imaging conditions.

(10) When actually imaging/measuring the EPs using the recipe created in a waferless condition without using the SEM device, the shape misfit between the pattern actually formed on the wafer and the pattern on the design data might be a problem. Therefore, according to another feature of the present invention, after automatically disposing the dimension measurement cursor on the SEM image of the EP in the item (1) described above, the shape misfit between the pattern in the SEM image and the pattern in the design data is calculated, thus correcting the position or the shape dimension measurement cursor based on the shape misfit information. According to the present processing, it becomes possible to correctly measuring the dimension even if the shape and the position of the actual pattern are different from those of the design data to a certain extent.

(11) Some of the items designated by the recipe cannot accurately be determined only with the design data. In the case, for example, of measuring the amount of recession of the line end section, although it is required to accurately detect the position of the line end section, in some cases, the corner sections of the pattern are rounded with respect to the mask pattern due to the resolution limit of the lithography. In the case in which there is a straight section with an enough length, it is possible to use an algorithm for detecting the line end section by applying the straight section. In the case in which a rounded section is dominant, it is possible to use an algorithm for detecting the line end section by applying the rounded section. However, there is a limit in estimating the extent of rounding of the line end section based only on the design data. Further, the extent of rounding can be varied in accordance with the variation in the manufacturing process. In order to solve such a problem, according to another feature of the present invention, a part of or the whole information of the dimension measurement method is changed based on the SEM image described above. The item (10) described above and the present item (11) are mechanisms for making the recipe, which is created based on the design data in the waferless condition, appropriately applicable to the real patterns.

(12) According to another feature of the present invention, at least one combination of the coordinates of the EP, the design data, the dimension measurement type/MP, the creation rule of the recipe, the recipe thus created, the image taken by the actual imaging sequence, the measurement result, and success and failure of one of the imaging and measurement is managed in a database while being associated with each other, thus making it possible to share the recipe among two or more SEM devices through a network or the like.

Then, the present invention will specifically be explained with reference to FIGS. 1 through 13.

1. SEM 1.1. Constituents of SEM

Figure 1:
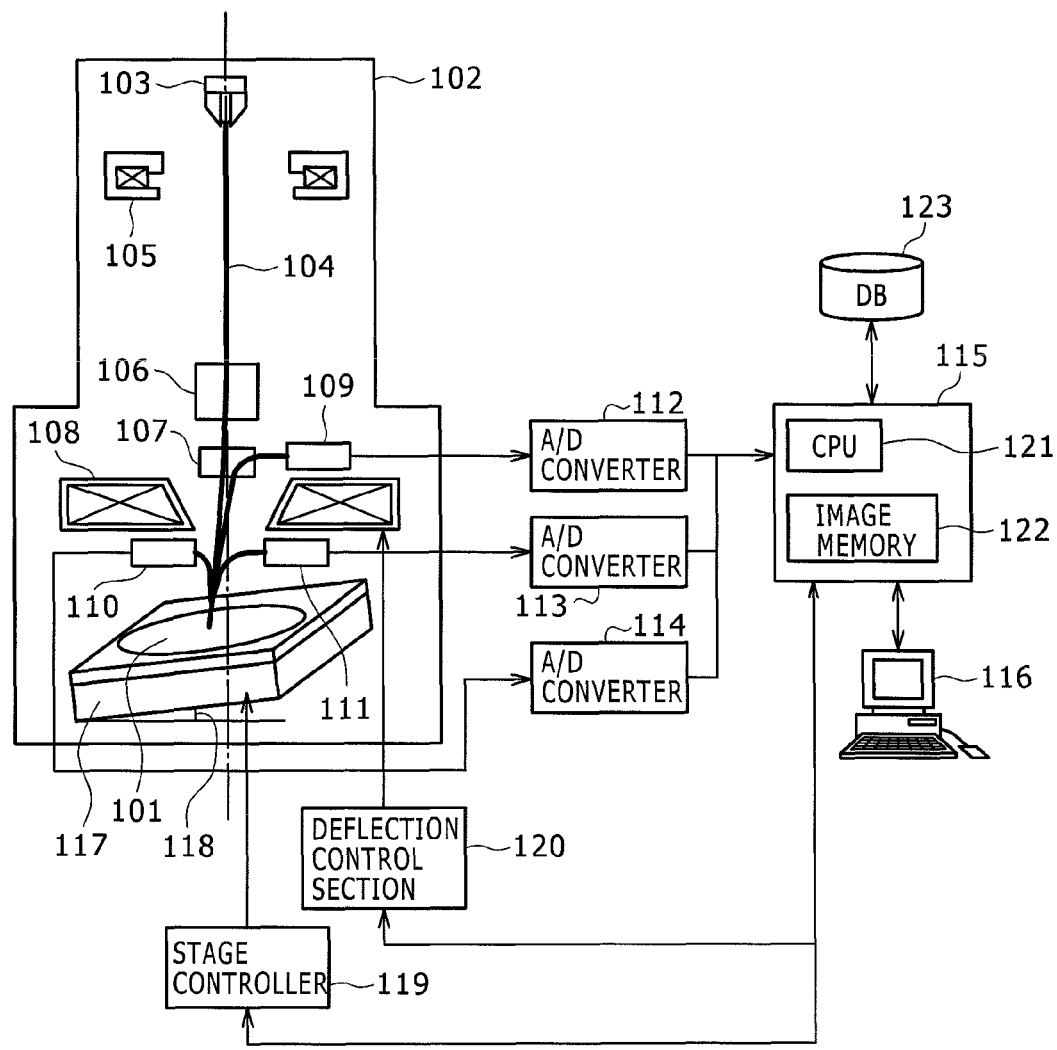
FIG. 1 is a diagram showing a configuration of an SEM device for embodying the present invention.

FIG. 1 shows a block diagram of a schematic configuration of a scanning electron microscope (SEM) for obtaining a secondary electron image (SE image) or a backscattered electron image (BSE image) of a sample according to the present invention. Further, the SE image and the BSE image are collectively called an SEM image. Further, the images obtained here include some or all of top-down images obtained by applying the electron beam in a vertical direction to the measurement object and tilted images obtained by applying the electron beam in a desired tilted direction.

An electron optical system 102 is provided with an electron gun 103 inside thereof, and generates an electron beam 104. The electron beam emitted from the electron gun 103 is condensed to be a narrower beam by a condenser lens 105. Then, a deflector 106 and an objective lens 108 control an application position and an aperture of the electron beam so that the electron beam is applied in a focused condition at a desired position on the semiconductor wafer 101 as a sample placed on a stage 117. Form the semiconductor wafer 101 irradiated with the electron beam, a secondary electron and a backscattered electron are emitted. A secondary-electron detector 109 detects the secondary electron moving along a path separated from the path of the applied electron beam by an ExB deflector 107. Meanwhile, backscattered-electron detectors 110, 111 detect the backscattered electron. The backscattered-electron detectors 110 and 111 are respectively disposed in directions different from each other. The secondary electron and the backscattered electron respectively detected by the secondary-electron detector 109 and the backscattered-electron detectors 110, 111 are converted by the A/D converters 112, 113, and 114 into digital signals, and the digital signals are input to the processing control section 115, stored in an image memory 122. A CPU 121 executes an image processing corresponding to a purpose on the digital signals.

Figure 2B:
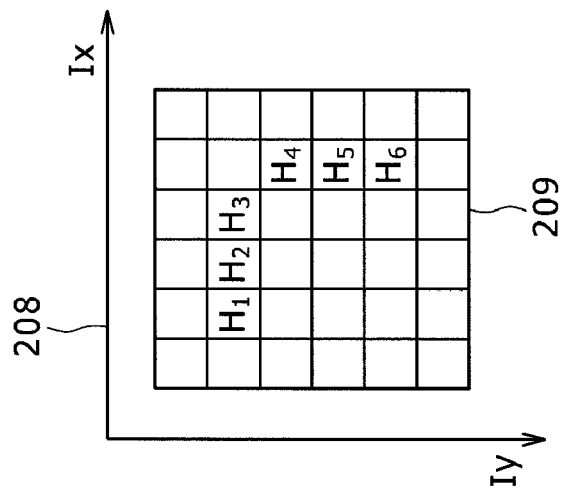
FIG. 2A is a diagram schematically showing the condition that electrons are emitted from a surface of a semiconductor wafer in response to scanning of an electron beam, and FIG.
Figure 2A:
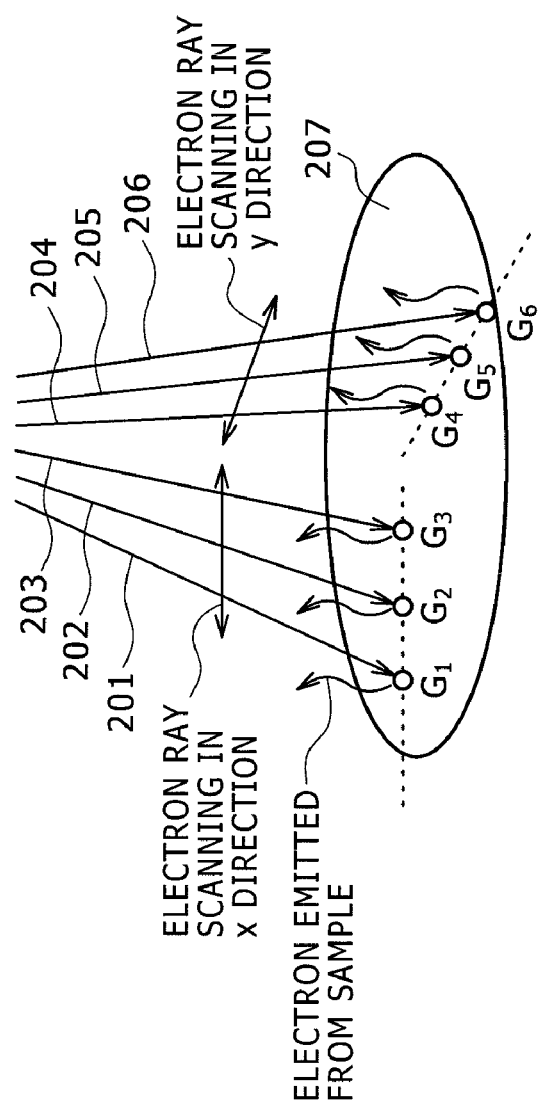

FIGS. 2A and 2B show a method of imaging the amount of signal of the electron emitted from the surface of the semiconductor wafer when the electron beam is applied on the semiconductor by scanning the electron beam thereon. The electron beam is applied while scanning in the x and y directions in a manner illustrated with the lines 201 through 203 and 204 through 206 as shown in, for example, FIG. 2A. It is possible to change the scanning direction by changing the deflecting direction of the electron beam. The positions on the semiconductor wafer at which the electron beam 201 through 203 scanned in the x direction are denoted with G1 through G3, respectively. Similarly, the positions on the semiconductor wafer at which the electron beam 204 through 206 scanned in the y direction are denoted with G4 through G6, respectively. The amounts of signals of the electrons emitted in the positions G1 through G6 correspond to the brightness values of pixels H1 through H6 in an image 209 shown in FIG. 2B, respectively (the subscripts 1 through 6 of G and H correspond to each other). The reference numeral 208 is a coordinate system indicating the x and y directions on the image. By thus scanning the inside of the view field with the electron beam, the image frame 209 can be obtained. Further, in reality, by scanning the inside of the view field with the electron beam several times in the same manner, and averaging the image frames thus obtained, an image with a high S/N can be obtained. The number of accumulated frames can be set according to needs.

The processing control section 115 shown in FIG. 1 is a computer system equipped with a CPU 121 and an image memory 122, and performs processing control such as sending control signals to a stage controller 119 or a deflection control section 120 based on the recipe in order to take images of the imaging points, or executing various kinds of image processing on the taken images at the desired imaging points on the semiconductor wafer 101. Here, the imaging points include some or all of an addressing point (hereinafter referred to as AP), an automatic focus adjustment point (hereinafter referred to as AF), an automatic astigmatism adjustment point (hereinafter referred to as AST), an automatic brightness/contrast adjustment point (hereinafter referred to as ABCC), and an evaluation point (hereinafter referred to as EP). Further, the processing control section 115 is connected to a processing terminal 116 (equipped with input/output means such as a display, a keyboard, and a mouse), and is provided with a graphic user interface (GUI) for displaying images to the user and accepting an input from the user. The reference numeral 117 denotes an XY stage for moving the semiconductor wafer 101, thereby making it possible to take images at desired positions on the semiconductor wafer. A change of the imaging position by the XY stage 117 is referred to as a stage shift. A change of the observation position by, for example, deflecting the electron beam with the deflector 106 is referred to as a beam shift. In general, the stage shift has characteristics of a large movable range and lower positioning accuracy of the imaging position, and in contrast, the beam shift has characteristics of a small movable range and higher positioning accuracy of the imaging position.

Although FIG. 1 shows an embodiment equipped with two detectors of the backscattered-electron image, it is possible to eliminate the detectors of the backscattered-electron image, or to decrease or increase the number of detectors of the backscattered-electron image.

The computer system 115 described above creates the recipe with the method described later, and controls the SEM device based on the recipe, thereby performing the imaging/measurement of the EP. It is possible to execute the processing control by sharing a part or the whole of the processing control with a plurality of separate processing terminals. The detail will be explained later with reference to FIGS. 12A and 12B. Further, the reference numeral 123 is a database storing coordinates of the EPs and design layout information (hereinafter referred to as design data) of a semiconductor circuit pattern formed on the wafer 101, which form an input to the computer system 115 for creating the imaging/measurement recipe. Further, it is also possible to store the measurement results and the recipes created in the computer system 115 for sharing the results and the recipes.

As the method of obtaining the tilted image of the measurement object observed in a desired tilted direction using the apparatus shown in FIG. 1, there can be cited (1) a method of deflecting the electron beam applied from the electron optical system to vary the application angle of the electron beam, thereby taking the tilted image (e.g., JP-A-2000-348658), (2) a method of tilting the stage 117 itself for moving the semiconductor wafer (the stage is tilted with a tilt angle 118 in FIG. 1), and (3) a method of mechanically tilting the electron optical system itself.

1.2. SEM Imaging Sequence

Regarding the imaging of the EP using the SEM described above, a supplementary explanation will be presented exemplifying the typical imaging sequence including the imaging of the AP, the AF, the AST, and ABCC shown in FIG. 3A.

Firstly, in the step 301 of FIG. 3A, the semiconductor wafer as a sample is attached on the stage 117 of the SEM device. In the step 302, by observing the global alignment mark on the wafer with the optical microscope or the like, origin misalignment of the wafer and rotation of the wafer are corrected.

In the step 303, the stage 117 is moved based on the control and processing of the processing control section 115 to move the imaging position to the AP for taking an image, a parameter for addressing is obtained, and then addressing is preformed based on the parameter thus obtained. Here, an explanation of the addressing will be added. In the case of observing the EP, if it is attempted to directly observe the EP using the stage shift, there is a possibility that the imaging position is significantly shifted due to the positioning accuracy of the stage. Therefore, the AP previously provided with the coordinates and the template (the pattern of the imaging point; either of the data formats of the SEM image and the design data can be adopted) of the imaging point is once observed for the purpose of positioning. The template is registered in the recipe, and therefore, hereinafter referred to as a registered template.

The AP is selected from the peripheral area (the range accessible with the beam shift) of the EP. Further, since the AP is generally a lower magnification view field compared to the EP, there is a low possibility that all of the patterns in the registered template becomes out of the view field with respect to a certain extent of the imaging position misalignment. Therefore, by matching the registered template of the AP and the SEM image (real imaging template) of the AP actually taken with each other, the amount of position misalignment at the AP can be estimated. Since the coordinates of the AP and the EP are know, the relative displacement vector between the AP and the EP can be obtained, and in addition, since the amount of the position misalignment of the imaging point at the AP can also be estimated by the matching described above, by subtracting the amount of the position misalignment from an amount of the relative displacement described above, the relative displacement vector from the imaging position of the AP to the EP, which should actually be traced, can be obtained. By moving the beam using the beam shift with a high positioning accuracy as much as the relative displacement vector described above, it becomes possible to take the image of the EP with a high coordinate accuracy.

In the step 304, based on the control and processing of the processing control section 115, the imaging position is moved to the AP using the beam shift, thus taking an image, a parameter for automatic focus adjustment is obtained, and then automatic focus adjustment is preformed based on the parameter thus obtained. Although in the flowchart shown in FIG. 3A, the automatic focus adjustment processing for taking a clear image of the EP is executed in the step 304, there can be adopted a variation such as setting the AF for taking a clear image of the AP in the same manner prior to the step 303, thereby executing the automatic focus adjusting processing using the AF prior to the AP imaging (the same applies to the AST, ABCC described later).

In the step 305, based on the control and processing of the processing control section 115, the imaging position is moved to the AST using the beam shift, thus taking an image, a parameter for automatic astigmatism adjustment (astigmatism correction) is obtained, and then automatic astigmatism adjustment is preformed based on the parameter thus obtained.

Then, in the step 306, based on the control and processing of the processing control section 115, the imaging position is moved to the ABCC using the beam shift, thus taking an image, a parameter for automatic brightness/contrast adjustment is obtained, and then automatic brightness/contrast adjustment is preformed based on the parameter thus obtained (in order to obtain a clear image with an appropriate brightness and contrast when taking the image of the EP, by adjusting the parameters such as the voltage value of the photomultiplier in the secondary-electron detector 109, the adjustment is executed so that the part with the highest image signal and the part with the lowest image signal show the full-contrast or the contrast close to the full-contrast).

Lastly, in the step 307, the imaging point is moved to the EP using the beam shift, and thus taking the image, and the dimension measurement of the pattern is performed with the measurement conditions thus determined.

FIG. 3B shows an example of the template positions of the EP 309, the AP 310, the AF 311, the AST 312, and the ABCC 313 on the beam shift allowable area from the EP with dotted frames. It should be noted that there can be variations in the steps 303, 304, 305, and 306 such as eliminating some or all of these steps, arbitrarily changing the order of the steps 303, 304, 305, and 306, or overlapping the coordinates of some of the AP, the AF, the AST, and the ABCC (e.g., the automatic focus adjustment and the automatic astigmatism adjustment are executed at the same position) according to the cases.

2. Flow of Automatic Recipe Creation Processing

The present invention relates to a method of automatically creating the recipe of the SEM. In order to achieve shortening of hours for creating the recipe and the reduction of incidence of the operator, improvement in the ratio of automation is essential, and to that end, it is a challenge that how automatically and quickly the recipe, which has a performance equivalent or superior to that of the recipe manually created by the operator, can be created. The processing flow according to the present invention will be explained using FIG. 4.

2.1. Data Input

Firstly, the coordinates of the EPs and the design data of the semiconductor circuit pattern are input (steps 401, 402, respectively). As the coordinates of the EPs, there are input the coordinates of hot spots (critical points) detected based on the result of, for example, an exposure simulation executed by an Electronic Design Automation (EDA) tool. Alternatively, in some cases, the coordinates of the EPs are input on a judgment of the user itself (taking the information of the EDA tool into consideration, if necessary). Further, in some cases, the attribute information of the EPs can also be obtained, or it is possible to input the attribute information if necessary (step 403). As the attribute information, a candidate of a possible defect at the EP (hereinafter referred to as a candidate defect) and so on can be cited. The candidate defect denotes a defect mode in which the patterns can be linked with each other at the EP (bridging), or the pattern can be narrowed or broken (necking), for example. It is possible to input the candidate defect with the highest possibility of occurrence referring to the analysis result by, for example, EDA tool, or to input the candidate defect the user wants particularly to avoid. It is possible to input a plurality of candidate defects for one of the EPs.

2.2. Dimension Measurement/MP Estimation Step

Subsequently, in the measurement recipe creation section 406, the dimension measurement type and the coordinates of the MP are estimated for each of the EPs (step 407). In order to create the dimension measurement cursor in the step 408 described later, it is required to know where the pattern to be measured exists in the EP, and what kind of measurement should be executed on the pattern to be measured. Regarding the estimation of the MP coordinates described above, although there are some cases in which the EP coordinates (the center coordinates of the EP area) match with the MP coordinates, there are also the cases in which they do not match with each other, or the cases in which two or more MPs exist in the EP. Further, even if the MP coordinates are provided by the input from the user, there is a possibility that the coordinate values include an error. Therefore, based on the coordinate data of the EP and the design data of the circuit pattern including the EP, the MP coordinates are estimated in the computer. Further, the dimension measurement types denote the variations of measurement at the MP, and as specific examples of the dimension measurement types, there are cited measurement of the line width of the line pattern, measurement of the gap between the line patterns, measurement of the amount of recession of the line end section, measurement of the diameter of the contact hole, measurement of the optical proximity correction (OPC) shape, and so on. Further, it is possible to include the information of a region to be measured such as the regions in the wiring area distance of which is measured in the dimension measurement type besides the category such as measurement of the line width. Further, it is also possible to include the information of a measurement direction such as a direction an amount of recession in which is measured in the measurement of "an amount of recession" in the dimension measurement type.

In the determination of the dimension measurement type/MP, taking the EP attribute information such as the candidate defects input in the step 403 into consideration, so as to reflect the managing intention of the user on the pattern shape at the EP, how the SEM, the measurement tool, measures the MP (i.e., the dimension measurement type) can be determined. As the estimation rule for estimating the dimension measurement type/MP in the computer, the default values related to the estimation rule and the processing parameters for the estimation prepared inside the system can be input for use if necessary (step 404). Further, the required specifications (e.g., specific requirements like "measurement of the region with as small design dimension as possible is preferable" or "measurement of a specific region is preferable with respect to a specific pattern") of the user regarding the dimension measurement type/MP are input if necessary, thus making it possible to create the estimation rule taking the required specifications into consideration (step 405).

2.3. Dimension Measurement Cursor Creation/Dimension Measurement Method Determination Step Subsequently, in the step 408, creation of the dimension measurement cursor, and selection or determination of the dimension measurement method are performed. In the creation of the dimension measurement cursor, the position and the shape of the dimension measurement cursor are determined on the design data (the dimension measurement cursor has the coordinates linking with the design data). Further, the determination of the dimension measurement method corresponds specifically to determination of the dimension measurement algorithm and the dimension measurement parameters. The selection or setting of the dimension measurement method is executed taking the information such as a dimension measurement type, or a shape or a direction of a pattern contour of the pattern to be measured into consideration if necessary.

2.4. SEM Imaging Conditions Determination Step

Subsequently, in the step 409, the imaging conditions of the SEM at the EP are determined. The SEM imaging conditions include at least the scanning direction of the electron beam. Although the raster scan is common in the two-dimensional scanning of the electron beam for creating the SEM image, the obtained SEM image is different between, for example, the case in which the scanning of the two-dimensional area is performed by executing continuous electron beam scanning in the x direction a plurality of times while shifting the scanning position discretely in the y direction, and the case in which the scanning of the two-dimensional area is performed by executing continuous electron beam scanning in the y direction a plurality of times while shifting the scanning position discretely in the x direction. Therefore, it is effective to automatically setting the scanning method with which the SEM image advantageous to the measurement taking the measurement region and the measurement direction in the EP into consideration. The scanning method is not limited to the scanning in the direction parallel to the x or y direction, but can have variations such as scanning in an oblique direction or scanning in the direction varying in accordance with the position in the EP.

2.5. EP Imaging Range/Coordinate Optimization Step

Subsequently, in the step 410, optimization of the imaging range and the coordinates of the EP are executed. The imaging range should be determined from the viewpoint that the measurement of the desired region in the MP is realized with appropriate measurement accuracy in addition to the viewpoint of the range the user wants to check. Therefore, it is necessary to set the imaging range so as to include at least the range of the dimension measurement cursor required from the viewpoint of measurement accuracy. Further, it is possible to change the coordinates of the EP provided by the user if necessary. The optimization of the EP coordinates includes principally three items, (a) changing the coordinates of the EP and the imaging range, (b) merging a plurality of view fields of the EPs to newly set a single EP, and (c) dividing one EP to set a plurality of EPs, and any combinations of these items. Specific examples of the contents of the processing and the advantages of the respective cases will be described below.

In the case of (a), if the position of the MP (or the imaging area including the dimension measurement cursor necessary for measurement) is found, it becomes possible to determine whether or not the center of the EP is shifted from the MP, and if it is shifted, it becomes possible to take the image of the MP at roughly the center of the view field of the EP by matching the view field of the EP with the center of the MP. Further, for example, it is possible to adjust the imaging range so that the range of the dimension measurement cursor is sufficiently included in the view field of the EP with respect to the imaging misalignment.

In the case of (b), when imaging/measuring dense continuous patterns in sequence, for example, in some cases, the imaging ranges set respectively to the patterns overlap with each other. In this case, there is a possibility that when taking an image of a certain EP, the contamination is caused in the measurement area included in another EP, thus degrading the measurement accuracy. Therefore, by resetting the EP area so that the patterns included in the respective EPs are collectively included in a single view field, the contamination in the measurement area described above can be prevented from occurring. When merging the EPs, the determination thereof can be made taking whether or not the dimension of the view field or the imaging magnification of the EP obtained by merging is within a predetermined dimension (since the measurement accuracy is generally lowered with the lower magnification) and whether or not the SEM imaging conditions (e.g., scanning direction of the electron beam) of the EPs to be merged match each other into consideration.

In the case of (c), if a plurality of MPs are included in the EP, and further, the directions of the patterns to be measured in the respective MPs are different from each other, and therefore, the SEM imaging conditions (e.g., the scanning direction of the electron beam) is required to be different between the MPs, it is effective to separate the MPs from each other as the EPs, thus taking images with the SEM imaging conditions different from each other. Further, in the case in which a number of MPs are included in the EP, and the MP is located closest to the edge of the view field of the EP, there is a possibility that a part of the measurement area of the MP runs off the view field due to the view field misalignment caused when taking the image of the EP. In such a case, division of the EP is effective.

2.6. Imaging Sequence Determination Step

Subsequently, in the imaging recipe creation section, the imaging recipe for taking the image of each of the EPs is created. Specifically, the determination of the imaging sequence including the setting of some or all of the adjustment points, the AP, the AF, the AST, the ABCC explained using FIGS. 3A and 3B is executed (step 412), and each of the templates of the adjustment points and the EP is registered in the recipe as the registered template if necessary (step 413). Further, based on the EP coordinates, the dimension measurement type, and the SEM imaging conditions determined in the measurement recipe creation section 406, the imaging order of the EPs is determined.

2.7. Imaging/Measurement Recipe Creation Step

In the step 414, the various parameters (the dimension measurement cursor, the dimension measurement method, the imaging sequence, the registered templates, and so on) determined in the measurement recipe creation section 406 and the imaging recipe creation section 411 are stored in the recipe (also referred to as the imaging/measurement recipe). Although in the embodiment, the items to be set in the imaging recipe and the measurement recipe, and the estimation procedures are separately explained, as described above, it is possible to manage the setting items designated by each of the recipes as a desired combination. By performing the processing based on the resign data, there is no need for taking an SEM image of a real wafer when creating the recipe on and before the step 414, and therefore, the operation can be carried out online, which leads to an improvement of the operation rate of the apparatus.

2.8. EP Imaging Step

Subsequently, in an imaging/measurement section 416, the imaging/measurement using a real wafer is performed. Firstly, the wafer is set in the SEM device (step 415), and the image of the EP is taken based on the recipe (step 417).

2.9. Dimension Measurement Cursor Disposition/Correction Step

Since the positional relationship between the SEM image of the EP and the corresponding design data can be obtained by actually taking the SEM image of the EP and matching the SEM image of the EP and the corresponding design data with each other, and the positional relationship between the dimension measurement cursor and the SEM image can also be obtained at the same time, the dimension measurement cursor can automatically be disposed on the SEM image (step 418). It should be noted that when actually imaging/measuring the EPs using the recipe created in a waferless condition based on the design data, the misfit of the shape between the pattern actually formed on the wafer and the pattern on the design data might be a problem. Therefore, after automatically disposing the dimension measurement cursor on the SEM image of the EP in the step 418, the shape misfit between the pattern in the SEM image and the pattern in the design data is calculated, thus correcting the position or the shape dimension measurement cursor based on the shape misfit information (step 419). According to the present processing, it becomes possible to correctly measuring the dimension even if the shape and the position of the actual pattern are different from those of the design data to a certain extent.

2.10. Dimension Measurement Method Changing Step

Similarly to the position and the shape of the dimension measurement cursor described above, some of the items designated by the recipe cannot accurately be determined only with the design data. In the case, for example, of measuring the amount of recession of the line end section, although it is required to accurately detect the position of the line end section, in some cases, the corner sections of the pattern are rounded with respect to the mask pattern due to the resolution limit of the lithography. In the case in which there is a straight section with an enough length, it is possible to use an algorithm for detecting the line end section by applying the straight section. In the case in which a rounded section is dominant, it is possible to use an algorithm for detecting the line end section by applying the rounded section. However, there is a limit in estimating the extent of rounding of the line end section based only on the design data. Further, the extent of rounding can be varied in accordance with the variation in the manufacturing process. In order to solve such a problem, a part of or the whole information of the dimension measurement method is changed based on the SEM image after obtaining the real SEM image if necessary (step 420). The steps 419, 420 are mechanisms for making the recipe, which is created based on the design data in the waferless condition, appropriately applicable to the real patterns. Although these steps are executed after the SEM imaging, these are correction of the setting items once determined offline, and do not require substantial processing time. Most of the processing is executed offline, and therefore, has no significant influence on the throughput of the SEM imaging.

2.11. Dimension Measurement Step

Using the dimension measurement cursor and dimension measurement method determined finally, the dimension measurement is performed using the SEM image at the EP (step 421). Further, if necessary, success and failure of the measurement is measured (step 422), and based on the result of the success and failure measurement, the recipe creation rule is changed in the step 427 described later if necessary. The determination of the success and failure of the measurement can be analyzed and managed with the categorized causes of failure such as (a) failure in imaging of (b) failure in measurement, further (a) can be categorized in further detail such as (a1) imaging misalignment caused by failure in addressing or (a2) blur of image caused by defocusing, and (b) can be categorized in further detail such as (b1) failure in dimension measurement type/MP estimation, (b2) misalignment of dimension measurement cursor, (b3) improper shape of dimension measurement cursor, or (b4) improper dimension measurement method.

2.12. Measurement Result Analysis/Recipe Creation Rule Optimization Step

Subsequently, in the measurement result analysis/recipe creation rule optimization section 423, based on the measurement result obtained in the step 421, the facture of the pattern is analyzed (step 424), and by performing the correction of the shape of the mask pattern or the modification of the semiconductor manufacturing process conditions, if necessary, a high yield ratio can be achieved (step 425).

Further, the recipe and the imaging/measurement result are analyzed (step 426) based on the recipe, the recipe creation rule, the determination result of the success and failure of the imaging/measurement and the information such as the cause of the failure obtained in the step 422 in the case of the failure in the imaging/measurement, and modification of the recipe creation rule is performed (step 427) if necessary.

At least one combination of the coordinates of the EP, the design data, the dimension measurement type/MP, the creation rule of the recipe, the recipe thus created, the image taken by the actual imaging sequence, the measurement result, and success and failure of one of the imaging and measurement is managed in a database while being associated with each other, thus making it possible to share the recipe among two or more SEM devices through a network or the like. In addition to the advantage that the necessity of creation of the recipe by every device can be eliminated, since the result data including successful cases and failed cases in the imaging/measurement obtained from a plurality of devices can be shared, it is possible to collect a lot of result data quickly, and if a problem exists in the recipe creation rule, for example, a measure against the problem can quickly be taken.

3. Detailed Explanations

Hereinafter, areas for which detailed explanations are necessary are extracted from the processing flow shown in FIG. 4, and supplementary explanations therefor will be presented.

3.1. Details of Dimension Measurement Type/Dimension Measurement Cursor/SEM Imaging Conditions The dimension measurement type, the dimension measurement cursor, and the SEM imaging conditions described in the steps 407 through 409 will be explained in detail with reference to FIGS. 6A through 6P. In FIGS. 6A through 6P, 601, 604, 608, 612, 615, 621, 624, 628, 632, 645, 648, 651, and 656 define the imaging ranges of the EP. As examples of the dimension measurement types, FIG. 6A shows the line width measurement of a line pattern 602, FIG. 6B shows the space measurement between line patterns 604 and 606, FIG. 6C shows the gap measurement between a line end section of a line pattern 609 and a line pattern 610, FIG. 6D shows the recession amount measurement (including expansion amount measurement) of a line end section of a line pattern 613, FIGS. 6E and 6F show the diameter measurement of contact holes 616, 622, respectively, FIG. 6G shows the major axis/minor axis measurement, FIG. 6H shows the gap measurement between line patterns 629 and 630, FIG. 6I is the shape measurement of a pattern 633 (specifically, the shape of the corner section indicated by a dotted frame 634). In the drawings, dotted frames 603A, 603B, 607A, 607B, 611A, 611B, 614, 617A, 617B, 618A, 618B, 619A, 619B, 620A, 620B, 623A, 623B, 626A, 626B, 627A, 627B, 631A, 631 B, 634 indicate the dimension measurement cursor. Further, the arrows illustrated together with the dotted frames indicate the places on which the dimension measurement is executed.

For example, in order to measure the line width, it is required to accurately and stably measure the positions of the right and left edges of the line. Therefore, an area (an area of the dimension measurement cursor, 603A or 603B in FIG. 6A) with a predetermined dimension including the edge is set on each of the right and the left edges, and a cumulative profile less subject to the image noise or the line edge roughness is obtained by accumulating the SEM signal in the area in the line direction, and the edge position is detected using the profile. The reference numeral 637 in FIG. 6K shows the SEM signal profile corresponding to the line between $\alpha$ and $\beta$ shown in FIG. 6A. In order to improve the S/N of the SEM signal profile 637 described above, it is also possible to use a profile obtained by averaging the SEM signal in the y direction in a length corresponding to, for example, the range (643) of the dimension measurement cursor.

In the SEM signal profile 637, the peak positions 638 of the right and left white bands are detected, and the distance between the peak positions 638 is measured as the line width. Although in the present embodiment, the distance between the peaks of the SEM signal profile is defined as the line width, there can be variations in the positions in the profile between which the distance is measured as the line width. For example, it is possible to obtain positions in the right and left white bands having a brightness value of X% of the difference between the peak brightness value and the brightness value of the substrate, and the distance between the positions thus obtained is measured (the parameter such as X% in the dimension measurement algorithm represented by the measurement described above is called a dimension measurement parameter). Examples of position or dimension parameters for determining the position and the shape of the dimension measurement cursor described above are shown in FIG. 6L, which is an enlarged diagram of FIG. 6A. As the parameters, there are cited arrangement positions of the dimension measurement cursors 640A and 640B, outside profile reference ranges 641A, 641B of the dimension measurement cursors 640A, 640B, disposed outside the line pattern 639, inside profile reference ranges 642A, 642B disposed inside the line pattern 639, and a profile accumulation ranges 643A, 643B. Thus, the line width 644 is accurately measured. The coordinates of the MP can be defined as, for example, the midpoint (or the midpoint of the line width 644) of the dimension measurement cursors 640A and 640B.

Further, in some cases, the dimension measurement cursors are set as a pair of dimension measurement cursors such as the pair of dimension measurement cursors 603A and 603B shown in FIG. 6A, and in other cases, the dimension measurement cursor is set as a single dimension measurement cursor such as the dimension measurement cursor 614 shown in FIG. 6D. Since in the case of FIG. 6D, the amount of recession of the line end section of the line pattern 613 is measured, the dimension measurement cursor is set so that the position of the line end section can accurately obtained by the SEM signal analysis inside the dimension measurement cursor 614.

In FIG. 6E, in order to measure the average hole diameter, the pairs of dimension measurement cursors are disposed at several positions in the circumferential area of the hole 616 (in the example shown in the drawing, four pairs of positions of 617A and 617B, 618A and 618B, 619A and 619B, and 620A and 620B), and the process such as averaging the diameter values thus measured is performed. It is also possible to measure the diameter at a pair of positions of the hole 622 with the dimension measurement cursors 623A, 623B as shown in FIG. 6F, and use the diameter thus measured as the representative value of the hole diameter.

In FIG. 6G, the minor axis of the pattern 625 is measured with the dimension measurement cursors 626A, 626B, and the major axis is measured with the dimension measurement cursors 627A, 627B, respectively. In the case of defining that the center of the dimension measurement cursors as the coordinates of the MP, the MP coordinates of the minor axis measurement and the major axis measurement are identical to each other. As described above, it is possible to set a plurality of dimension measurement types with respect to a single MP coordinate.

In FIG. 6I, in order to perform the evaluation of the facture of the contour of a two-dimensional pattern, dense shape gap vectors 636 between the pattern 633 on the SEM image and the design data 635 displayed in an overlaying manner on the pattern on the SEM image are obtained as shown in FIG. 6J, the enlarged view of the area 634 indicated in FIG. 6I. As described above, the measurement of a plurality positions is also possible instead of measurement of one of a plurality of positions. Further, there can be cited a measuring method of quantizing the degree of rounding of a corner, for example, based on the measurement values of the plurality of positions, and outputting the quantized value as one of evaluation values. Further, the measurement value is not limited to the distance between desired two regions of the patterns on the SEM image, but it is possible to use the misfit amount between the design data and the pattern on the SEM image at a desired region as the measurement value, for example, as described above.

As described above, the difference in the type of the pattern and the region on which the cursor is disposed is categorized as the dimension measurement type.

Further, it is possible to include the information of the measurement direction in the dimension measurement type. FIG. 6M shows an example of measuring the line width of the line pattern 646 extending in the y direction, namely the dimension in the x direction, FIG. 6N shows an example of measuring the line width of the line pattern 649 extending in the x direction, namely the dimension in the y direction. Such information of the measurement direction becomes the information necessary for determining the SEM imaging conditions in the step 409 shown in FIG. 4 described later. A determination method of the scanning direction of the electron beam, which is one of the SEM imaging conditions, will be explained as an example. Since in FIG. 6M the dimension in the x direction is measured, it is desirable to scan the electron beam continuously in the x direction. Therefore, as schematically shown in the drawing, it is possible to obtain the image by executing the continuous electron beam scan 647 in the x direction a plurality of times while shifting the scan line discretely in the y direction (in the drawing, the number of times of shifting is schematically set to four times). Since in FIG. 6N the dimension in the y direction is measured, similarly, in this case, it is possible to obtain the image by executing the continuous electron beam scan 650 in the y direction a plurality of times while shifting the scan line discretely in the x direction. As described above, owing to the information of the measurement direction, appropriate SEM imaging conditions can be determined. The reference numerals 662A, 662B is FIG. 6M, and 663A, 663B in FIG. 6N respectively denote the dimension measurement cursors.

3.2. Details of Dimension Measurement Type Estimation/MP Estimation

The dimension measurement type estimation/MP estimation described in the step 407 will be explained in detail with reference to FIG. 5. In order to automatically create the dimension measurement cursor, it is necessary to know the dimension measurement type/MP in the ER In other words, the dimension measurement cursor can hardly be set without understanding what deformation of the pattern possibly occurs at which place, and what dimensional value needs to be measured/controlled with respect to the deformation. Further, it is not easy for the user to manually designate all of such dimension measurement types. Therefore, the dimension measurement types/MP are estimated inside the computer based on the coordinate data of the EPs and the design data of the circuit pattern including the EPs, and the dimension measurement cursor is created based on the dimension measurement types/MP thus estimated. Firstly, the EP is selected in the step 501 shown in FIG. 5. The design data corresponding to the area including the EP is input in the step 508, and the candidate of the dimension measurement type/MP is refined in the step 502. Here, if the candidate of the dimension measurement type/MP is determined (in the case in which the determination of the "DIMENSION MEASUREMENT TYPE/MP DETERMINED?" in step 503 is Yes), the process proceeds to step 504. If the candidate of the dimension measurement type/MP is not determined (in the case in which the determination of the "DIMENSION MEASUREMENT TYPE/MP DETERMINED?" in step 503 is No), warning is sent to the user via the GUI or the like (step 514). The user can change the estimation rule of the dimension measurement type/MP referring to the example in which the dimension measurement type has not been determined appropriately.

FIG. 7A shows patterns 702, 703 on the SEM image included in the view field 701 of the EP, as an example. FIG. 7B shows the design data corresponding to the EP, and the patterns on the design data corresponding to the patterns 702, 703 are 704, 705, respectively. The examples of the candidate of the MP coordinate estimated from the design data are cited as 708, 710, 712, 714, 716, and 718 in FIGS. 7D through 7G, respectively. From the viewpoint of the dimension measurement type, the MP 708 corresponds to the measurement of the line width of the line pattern in the x direction at the region measured by the dimension measurement cursors 709A, 709B, the MP 710 corresponds to the measurement of the line width of the line pattern in the x direction at the region measured by the dimension measurement cursors 711A, 711B, the MP 712 corresponds to the measurement of the amount of recession in the line end section in the y direction at the region measured by the dimension measurement cursor 713, the MP 714 corresponds to the measurement of the amount of recession in the line end section in the y direction at the region measured by the dimension measurement cursor 715, the MP 716 corresponds to the measurement of the gap between the line patterns at the region measured by the dimension measurement cursors 717A, 717B, and the MP 718 corresponds to the measurement (the measurement of the rounding of the corner or the like) of the OPC shape at the region measured by the dimension measurement cursor 719.

As described above, a plurality of candidates of the dimension measurement type/MP exists in the single EP, and the dimension measurement type/MP, which the user actually wants to measure, may be one of the candidates described above, or may be a combination of the candidates. Therefore, in the estimation of the dimension measurement type/MP to be actually measured, at each of the pattern regions included in the circuit design pattern including the EPs, attribute information composed of at least one combination of a candidate of the dimension measurement type, a candidate of a possible defect, a circuit attribute, easiness of deformation, measurement dimension on the design data, and the distance from the center of the EP is calculated, and the candidate of the dimension measurement type/MP at the EP is extracted along the estimation rule based on the attribute information. By taking a plurality of pieces of attribute information into consideration, the automatic estimation of the dimension measurement type/MP with high accuracy becomes possible.

Further, as described above, the estimation rule of the dimension measurement type/MP can be determined taking the attribute 509 (corresponding to 403 shown in FIG. 4) of the EP, the default values 510 (corresponding to 404 shown in FIG. 4), and the user required specification 511 (corresponding to 405 shown in FIG. 4) into consideration if necessary. Further, as a mechanism for reflecting the difference in the setting criteria of the dimension measurement type/MP between the users, it is possible to input the dimension measurement type/MP estimation rule designated by the user (step 512). It should be noted that the creation of the estimation rule is generally a difficult work for the user. Therefore, as the mechanism for easily performing the user customization, it is possible that, in response to the user performing at least one combination teaching of the EP and the position of the MP in the EP, or a combination teaching of the EP and the dimension measurement type in the EP (step 513), the estimation rule is optimized inside the system based on the teaching, thus the general estimation rule can automatically be created.

When the dimension measurement type/MP is determined, the dimension measurement cursor creation/dimension measurement method determination is performed in the step 504, and the determination of the SEM imaging conditions is performed in the step 505 if necessary. The processing of the steps 501 through 505 are executed repeatedly with respect to all of the EPs to be imaged (determination of the termination is made in the step 506), then in the step 507, optimization of the EP imaging range/coordination is performed (corresponding to the step 410).

Incidentally, the estimation of the dimension measurement type/MP or the creation of the dimension measurement cursor is effectively performed based on the pattern similar to the shape of the real pattern formed on the wafer as much as possible. Therefore, it is possible to perform the estimation or the creation using the patterns 706, 707 (hereinafter referred to as modified design data) obtained by modifying the patterns 704, 705 on the design data shown in FIG. 7. As the method of generating the modified design data, there can be cited a method of generating the modified design data using litho-simulator on the design data, and a method of generating the modified design data by the shape modification briefly simulating the litho-simulator. The modified design data 706, 707 in the drawing is an example of rounding the corner sections of the design data 704, 705 assuming that the corner sections of the pattern are rounded due to the resolution limit of the lithography.

3.3. Details of EP Imaging Range/Coordinate Optimization

A specific example of the EP imaging range/coordinate optimization described in the step 410 will be explained with reference to FIG. 8. FIG. 8A shows an example in which the user wants to measure the line width of each of the six line patterns 802 through 807. The MPs disposed on the six line patterns are 808 through 813, respectively. FIG. 8B shows the EPs 814 through 819 having the view fields set correspondingly to the centers of the MPs so that the measurement in each of the line patterns becomes possible. However, if the EPs are set as shown in FIG. 8B, the imaging ranges of the EPs overlap with each other, and when taking the image of one of the EPs, contamination is caused in the measurement area included in another of the EPs, there is a possibility of degrading the measurement accuracy. Therefore, it is possible to optimize the imaging range of the EP as illustrated as the EPs 820, 821 shown in FIG. 8C. In the present embodiment, the MPs 808 through 810 can be measured using the EP 820, and the MPs 811 through 813 can be measured using the EP 821, and moreover, there is no overlapping area between the EPs 820, 821. Further, the number of times of imaging can also be reduced from six in the case with the EPs 814 through 819 to two in the case with the EPs 820, 821. Incidentally, from the viewpoint of the number of times of imaging, it is possible to include entire area 801 in one EP. However, in such a case, there is a possibility of degrading the measurement accuracy because the magnification is lowered. Therefore, it is necessary to set the EP imaging range or the EP coordinates taking the overlapping of the ranges, the number of times of imaging, the measurement accuracy, and so on into consideration, and achieving a balance therebetween.

Further, in the optimization of the EP imaging range/coordinates, it is necessary to take the SEM image conditions in the EP into consideration. FIGS. 8D through 8F show examples of optimizing the EP imaging range/coordinates based on the scanning direction of the electron beam out of the SEM imaging conditions. In FIG. 8D, there are disposed three MPs 825, 828, and 830 on the design data 823 and 824, and the EPs 832, 833, and 834 including the respective MPs are set as an initial condition. Out of the three MPs, the MPs 825, 828 correspond to the line width measurement in the x direction, and as shown in FIG. 6M, it is desirable to perform the continuous scan in the x direction, and the discrete scan in the y direction. In contrast, the MP 830 corresponds to the line width measurement in the y direction, and as shown in FIG. 6N, it is desirable to perform the continuous scan in the y direction, and the discrete scan in the x direction. Therefore, it is necessary to perform the SEM imaging on the MPs 825, 828, and the MP 830 with different imaging conditions, and therefore, it is not allowed to merge the both parties into the same EP. Therefore, for example, as shown in FIG. 8E, it is possible to merge the MP 825 and MP828 into a single EP 835, and to take the image of the MP 830 as a single EP 836. In contrast, as shown in FIG. 8F, in the case in which the MP 825 corresponds to a single EP 837, and the EP 838 into which the MPs 828, 830 are merged is provided in the initial condition, it is possible to separate the both MPs to two EPs based on the determination criteria described above. As describe above, for the optimization of the imaging range of the EP, and integration/separation of the EP, it is effective to use the information of the dimension measurement type, MPs, and the dimension measurement cursors (826A, 826B, 829A, 829B, 831A, and 831B).

Incidentally, it is necessary for the imaging range to appropriately include the measurement area (the area of the SEM image required to perform the measurement), and it is preferable that the measurement area is included in the view field even if there is some imaging misalignment. An explanation will be presented exemplifying FIGS. 6O and 6P. FIG. 6O shows an example of the line width measurement of the line pattern 652, and the dimension measurement cursors are denoted as 653A, 653B. Regarding the setting of the imaging range of the EP, it is required to include at least the dimension measurement cursors 653A, 653B, and in the case in which there is a possibility that the view field shift is caused in the x direction with a distance 654, it is desirable that the imaging range 655 includes the measurement area even if the imaging range 651 is shifted as much as the distance 654 to become the imaging range 655. In this example, no problem occurs with respect to the amount of view field shift of 654. On the other hand, FIG. 6O shows an example of measurement of the gap between the patterns 657 and 658. Although the dimension measurement cursors 659A, 659B are included in the imaging range 656 similarly to the example of FIG. 6O, in the case in which the imaging range is shifted to 661 in accordance with the amount of position shift 660 identical to the amount of the position shift 654 described above, a part of the dimension measurement cursor runs off the view field. As described above, it is effective to determine the imaging range based on the range of the dimension measurement cursor and the expected value of the view field shift.

3.4. Details of Imaging Sequence Determination

In the imaging sequence determination described in the step 412, a specific example of determination of the imaging order of the EPs will be explained with reference to FIGS. 11A through 11E. FIG. 11A shows an example in which eight EPs exist in an area with low magnification, and the eight EPs are denoted as EP[1] through EP[8], respectively. In the view field of each of the EP[1], EP[3], EP[5], and EP[7], there are included three line patterns extending in the x direction, and these EPs are collectively called EP group 1. In the view field of each of the EP[2], EP[4], EP[6], and EP[8], there are included three line patterns extending in the y direction, and these EPs are collectively called EP group 2. The EPs belonging to the EP group 1 correspond to the line width measurement in the y direction, and the scanning direction of the electron beam as illustrated with the arrows 650 shown in FIG. 6N is preferable. In contrast, the EPs belonging to the EP group 2 correspond to the line width measurement in the x direction, and the scanning direction of the electron beam as illustrated with the arrows 647 shown in FIG. 6M is preferable. Therefore, in the case in which the EP belonging to the EP group 2 is imaged after the EP belonging to the EP group 1 has been imaged, or the EP belonging to the EP group 1 is imaged after the EP belonging to the EP group 2 has been imaged, it is required to execute a rotation of the view field or the beam scan. In the light of the above, optimization of the imaging order will be considered. As shown in FIG. 11B, the initial imaging order (input by the user, for example) is sequentially from the EP[1] to the EP[8]. In contrast, with intent to reduce the number of rotation, for example, as shown in FIG. 11C, starting with the imaging of the EP group 1, the order will be EP[1]→EP[3]→EP[5]→EP[7]→EP[2]→EP[4]→EP[6]→EP[8]. It should be noted that in order to reduce the total distance of view field movement between the EPs thereby improving the throughput, as shown in FIG. 11D, the order will be EP[1]→EP[5]→EP[7]→EP[3]→EP[2]→EP[6]→EP[8]→EP[4] (because the distance between the EP[1] and EP[5] is shorter than the distance between EP[1] and EP[3]). It should be noted that if the time required for rotation is extremely shorter than the time required for the view field movement between the EPs, it is possible to adopt the order shown in FIG. 11B giving weight to the reduction of view field movement. Further, if the time required for the rotation and the time required for view field movement are equivalent to each other, the imaging order shown in FIG. 11E can also be adopted taking the both into consideration (the number of times of rotation is smaller than that shown in FIG. 11B, and the view field movement distance is shorter than that shown in FIG. 11D). As described above, the imaging order of the EPs are determined based on the EP coordinates or the SEM imaging conditions including at least the scanning direction of the electron beam in the EPs.

3.5. Details of Dimension Measurement Cursor Correction

A specific example of the dimension measurement cursor correction described in the step 419 will be explained with reference to FIGS. 9A through 9K. The present drawings related to the examples for correcting (A) the distance 906 between the dimension measurement cursor, (B) the outside profile reference ranges 903A, 903B located outside the line pattern 901 based on the design data, and (C) the arrangement positions of the overall dimension measurement cursor among the various position and dimension parameters for determining the dimension measurement cursor, and other dimension parameters can also be corrected in a substantially the same manner. Further, in order to achieve consistency in the measurement values with the EPs, it is possible to perform setting so as not to perform correction of some or all of the position and dimension parameters (if, for example, the profile accumulation range 905A, 905B become different between the EPs, there is a possibility that the measurement become unable to be compared to each other.

(A) Correction of Distance Between the Dimension Measurement Cursors

FIG. 9A shows the dimension measurement cursors 902A, 902B disposed on the design data 901 in the step 408 shown in FIG. 4. The inside of each of the dimension measurement cursors 902A, 902B is divided into two ranges, namely an outside profile reference range 903A, 903B located outside the line pattern 901 based on the design data and an inside profile reference range 905A, 904B located inside the line pattern 901 based on the design data. The object is to measure the line width in the x direction of the line pattern 907 observed with the SEM, and shown in FIG. 9B. Firstly, as shown in FIG. 9C, matching of the pattern 907 on the SEM image and the design data 901 is performed, and as shown in FIG. 9D, the dimension measurement cursors 902A, 902B are disposed on the SEM image. Here, the pattern 907 on the SEM image has a line width extended largely (in the drawing, it is extended to be the widths 908A, 908B larger than the design data 901) compared to the design data 901, the positions of the dimension measurement cursors arranged assuming the line width on the design data are shifted from the edge positions of the pattern on the SEM image. Therefore, as shown in FIG. 9E, it is possible to successfully measure the line width by shifting the position of the dimension measurement cursors in accordance with the edge positions (the distance 906 between the dimension measurement cursors is increased to 909).

(B) Correction of Outside Profile Reference Range Located Outside the Pattern

In FIG. 9E, reference numeral 910 denotes the SEM signal profile corresponding to the line traversing the line pattern 907, and extending between α and β. In the line width measurement, there is used an algorithm of obtaining, for example, the positions each having the brightness value of X% of the difference between the peak brightness value and the brightness value of the substrate in the right and left white bands (corresponding roughly to the right and left edges of the line pattern) of the SEM signal profile 910, and then measuring the distance between the positions. In order to execute such various kinds of profile analysis, it is required for the measurement range (the range of the dimension measurement cursors) on which the analysis is executed to sufficiently include the protrusions of the white bands. Although the outside profile reference ranges 903A, 903B located outside the line pattern 907 are set a little bit longer with a margin, in the real SEM signal profile 910, the skirt section of the white band protrusions is longer than expected, and further, it has proved that the profile must be analyzed in the range the width 911A, 911B larger than expected. On this occasion, by correcting the outside profile reference ranges 903A, 903B located outside the line pattern 907 so as to be extended to be 912A, 912B as shown in FIG. 9F, it becomes possible to successfully measure the line width.

(C) Correction of Arrangement Positions of Overall Dimension Measurement Cursor

The reference numeral 912 shown in FIG. 9G denotes the design data of the upper layer pattern, and the reference numeral 913 denotes the design data of the lower layer pattern. The reference numerals 914A, 914B denote the dimension measurement cursors, and are disposed so as to measure the line width 915 of the upper layer pattern 912 in the area where the upper layer pattern 912 and the lower layer pattern 913 intersect with each other. This corresponds to the request, for example, that it is necessary to measure the line width in the active area of the gate exerting a significant influence on the apparatus characteristic. FIG. 9H shows the patterns 916, 917 on the SEM image corresponding respectively to the patterns 912, 913 on the design data. Since the pattern 917 is located in the lower layer of the pattern 916 with respect to the stacking direction of the pattern, there is cause a hidden part in the area where the both layers overlap with each other. FIG. 9I shows an example in which the pattern on the wafer and the design data are matched with each other, and the dimension measurement cursors 914A, 914B are arranged on the pattern. In the present example, the arrangement result of the dimension measurement cursors is preferable. In contrast, FIG. 9J shows an example in which the upper layer pattern 916 (corresponding to the design data 912) and the lower layer pattern 919 (corresponding to the design data 913) are shifted from each other (the amount of shift is denoted as 918) due to a failure of the manufacturing process. FIG. 9J shows the result of matching executed so that the pattern on the wafer and the design data match with each other with respect to the upper layer pattern, and as a result, there arises a problem that the dimension measurement cursors are disposed at the positions shifted a little from the positions where the upper layer pattern and the lower layer pattern overlap with each other, and on which the measurement is originally required to be executed. Therefore, as shown in FIG. 9K, by matching the lower layer pattern 921 (corresponding to the pattern 913) with the pattern 919 on the SEM image independently from the upper layer pattern 912, and disposing the dimension measurement cursors 920A, 920B (corresponding to the dimension measurement cursors 914A, 914B) in conjunction with the position of the lower layer pattern 921, the measurement on the desired place is realized. As described above, it is required to dispose the dimension measurement cursors appropriately based on the intent of the user on the measurement.

3.6. Details of Change of Dimension Measurement Method

A specific example of the change of the dimension measurement method described in the step 420 will be explained with reference to FIG. 10. The dimension measurement method denotes specifically the dimension measurement algorithm and the dimension measurement parameters. FIG. 10A shows two patterns 1001, 1002 on the design data and the dimension measurement cursors 1003A, 1003B for measuring the distance 1004 between the two patterns described above. FIG. 10B shows a matching result between the patterns 1005, 1006 on the SEM image and the design data described above, and FIG. 10C is an enlarged view in the vicinity of the dimension measurement cursor 1003B. As an image processing algorithm for detecting the end section of the pattern 1002 with good accuracy after applying the dimension measurement cursors, it is possible to adopt an algorithm of detecting the end section by applying the straight lines, providing the end section has enough straight line section. The five x marks 1007 shown in FIG. 10C represent characteristic points of the end section detected from the SEM image, and by applying straight lines to the characteristic points, it becomes possible to stably detect the end section with respect to the variation in the shape of the end section (the straight line 1008 is applied). Meanwhile, FIG. 10D shows an example in which the corner sections of the patterns 1009, 1010 (corresponding to the patterns 1005, 1006) are rounded significantly due to the resolution limit of the lithography in the similar measurement example, and FIG. 10E is an enlarged view in the vicinity of the dimension measurement cursor 1003B. In contrast to the straight line application algorithm described above, in the case in which the rounded section is dominant as the characteristic points 1011 in the end section, an algorithm for detecting the end section by applying curved line is effective (the curved line 1012 is applied). As described above, for example, in some cases, the degree of rounding in the end sections cannot accurately estimated only with the design data. In order to solve such a problem, a part of or the whole information of the dimension measurement method is changed based on the SEM image described above.

4. System Configuration (Database Management/Sharing)

An embodiment of a configuration of an apparatus according to the present invention will be explained with reference to FIGS. 12A, 12B. In FIG. 12A, the reference numeral 1201 denotes a mask pattern designing device, the reference numeral 1202 denotes a mask drawing device, the reference numeral 1203 denotes an exposure/development device, the reference numeral 1204 denotes an etching device, the reference numerals 1205 and 1207 denote SEM devices, the reference numerals 1206 and 1208 denote SEM control devices for respectively controlling the SEM devices, the reference numeral 1209 denotes an Electronic Design Automation (EDA) tool server, the reference numeral 1210 denotes a database server, the reference numeral 1211 denotes a storage for storing a database, the reference numeral 1212 denotes an image processing and imaging/measurement recipe creation calculation device, the reference numeral 1213 denotes an imaging/measurement recipe server, the reference numeral 1214 denotes a shape measurement/evaluation tool server for the created pattern, and these constituents are capable of communicating information via a network 1220. The database server 1210 is provided with the storage 1211 attached thereto, and some or all of (a) coordinates of EPs, (b) design data, (c) dimension measurement type/MP, (d) creation rule of recipe (including estimation rule of dimension measurement type/MP), (e) recipe created, (f) image taken along the actual imaging sequence, (g) measurement results, (h) success and failure of imaging or measurement, and (i) cause of failure of imaging or measurement can be stored and retrieved in conjunction with model, manufacturing process, data acquisition device.

Further, although in the drawing, the two SEM devices 1205, 1207 are connected to the network, for example, in the present invention, it is possible for an arbitrary number of SEM devices to share the imaging/measurement recipes by the database server 1211 or the imaging/measurement recipe server 1213, and it is possible to operate the plurality of SEM device by a single imaging/measurement recipe creation. Further, by sharing the database among the plurality of SEM devices, the success and failure of the imaging or measurement and the causes of the failure in the past can quickly be accumulated, and by retrieving the records, some help is obtained for creating preferable imaging/measurement recipes.

FIG. 12B shows an example of integrating the SEM control devices 1206 and 1208, the EDA tool server 1209, the database server 1210, the image processing and imaging/measurement recipe creation calculation device 1212, the imaging/measurement recipe server 1213, and the shape measurement/evaluation tool server 1214 shown in FIG. 12A into a single device 1216. As described in the present example, it is possible to divide any desired functions into an arbitrary number of devices, or to integrate any desired functions for execution.

5. GUI

FIG. 13 shows an example of GUI for performing the setting and display of input/output information in the present invention. The various pieces of information drawn in the inside of the window 1300 in FIG. 13 can be displayed on a display screen in one frame or divided into several frames. Further, "*" in FIG. 13 represents a certain number (character string) or a range of a numerical value input to the system or output therefrom.

In the window 1320, 1321, the recipe creation rule is designated if necessary. It is possible to input default values. In the recipe creation rule, the windows 1320, 1321 specifically displays the parameters for setting the dimension measurement type/MP estimation rule, for example, it is possible to set the estimation rule based on the attribute information (candidate of the dimension measurement type, candidate of possible defect, circuit attribute, easiness of deformation, measurement dimension on the design data, distance from the center of the EP, etc) obtained in each of pattern regions. In other words, if there is a numerical value requirement needs to be satisfied by each of the pieces of attribute information of the finally selected dimension measurement type/MP with respect to the plurality of dimension measurement type/MP included in the EP, the numerical value is input in the window 1320. Further, if there is the attribute information needs to be evaluated with importance in estimating the dimension measurement type/MP, it is possible to input the evaluation weight in the window 1321.

In the windows 1324, 1325, and 1337, there is displayed information of a plurality of recipes. As the information displayed on each of the windows 1324, 1325, and 1337, the user can input a designated value, the value prepared inside the system can be provided as the default value, or the recipe creation engine inside the system can estimate and output. Hereinafter, the displayed contents will be explained specifically picking up the EP whose ID displayed in the "EP ID" column is 1 (note that the corresponding items in the EP whose ID is 2 is described in the parenthesis).

In the window 1325, there are displayed a circuit pattern 1326 (1332) in the EP (a SEM image, the design data, or both of them), the dimension measurement cursors 1327, 1328 (1333), the imaging sequence 1329 (1334) for imaging the EP (e.g., the coordinate of the adjustment points, the range/shape, and the imaging conditions, although in the drawing, the order is set as AP1→AP2→AF→EP (in the case with ID=2, AP→AST→AF→EP), the adjustment templates passed through are different between the EPs), information 1330 (1335) related to the EP (the coordinates of the EP, the range/shape, the imaging conditions, etc), the information 1331 (1336) related to the MPs in the EP (the coordinates, the dimension measurement type, the coordinates/dimension/shape of the dimension measurement cursor, the dimension measurement method). It is possible to display the attribute information 1338 (1339) on the window 1337. If a plurality of MPs exists in the EP, the information of the MP such as the information 1331 (1336) related to the MP, the attribute information 1338 (1339) in the MP, it is possible to display the information for each of the MPs.

A part of or whole information is determined in response to pressing the recipe creation button 1322. Further, although in the windows 1324, 1325, 1337, the information related to the plurality of EPs is displayed vertically in the order of the ID, it is possible to sort the display order of the EPs with a desired criteria, or limit the EP to be displayed. The desired criteria can be designated using a pull-down menu 1323. As examples of the criteria, there can be cited (a) displaying the EPs in ascending order of the estimation accuracy of the dimension measurement type/MP (the reliability of the estimation is calculated in the dimension measurement type/MP estimation, and sorting is executed based on the reliability), (b) eliminating the EP failed to estimate the dimension measurement type/MP from displaying (e.g., the EP causing the warning in the step 514 shown in FIG. 5), (c) eliminating the EP, whose position/dimension/shape have been changed, from displaying (e.g., the EP having the state changed from the initial state provided by the user by changing the imaging range, merging with another EP, or dividing), (d) displaying only the EP including a plurality of MPs. By sorting the information from a plurality of viewpoints as described above, when a problem occurs in a recipe, or when a problem may occur, it becomes possible to execute GUI display while sorting the cause of the problem based on the cause, thus problem analysis and correction can efficiently be executed.

The imaging sequence 1329 can be visualized and then displayed on the window 1301. On the window 1302, the imaging sequence for imaging the EP with the ID of "first" is visualized as AP1 (1303)→AP2 (1304)→AF (1305)→EP 1306). Further, the display method in the window 1301 can be provided with a several options. As examples of such options provided to the display method, there are cited a designation (check box 1317) of the stacked layer to be displayed, a switching option (check box 1318) for switching the display of the coordinate gauge displayed in the frame 1302 between the relative coordinate from the EP and the absolute coordinate (from a certain reference point), designation of the display magnification (1319), and so on.

Further, the window 1307 shows the table of the EPs. In the window, the reference numerals 1308 through 1311 denote the initial EPs designated by, for example, the user, and by pressing the optimization button 1316, if necessary, for example as shown in FIG. 8, change of the imaging range of the EP, merging of a plurality of EPs, or division of the EP is executed. The reference numerals 1312 through 1315 are optimized EPs. From the viewpoint of the relationship between the EPs before the optimization and the EPs after the optimization, it is understood, for example, that the EP1 (the EP with the first ID) before the optimization and the EP2 (the EP with the second ID) before the optimization are merged into a new EP1. Further, by checking the check box displayed on the left of the display of the EPs 1308 through 1315, it is possible to display the EP, which is provided with the check, in the window 1301.

It should be noted that although in the embodiments described above, the recipe creation in the SEM device is explained, the present invention can be applied not only to the SEM devices, but also to optical microscopes, scanning probe microscopes (hereinafter referred to as SPM), and so on. In other words, in the optical microscope or the SPM, there are some cases in which the desired EP is observed, and the measurement is executed on the MP in the EP, and therefore, the automatic recipe creation method, the data managing method, and the system configuration, the GUI, and so on described in the present invention can be utilized therefor. In the SPM, the SEM image described in the embodiments is replaced with the depth information obtained by the SPM or the image obtained by converting the depth information (by converting the depth value into the brightness value).

Due to the reduction of design margin associated with the miniaturization and density growth of the LSI, the number of evaluation points at which the dimensional control of the semiconductor pattern is required is dramatically increasing, and the improvement in the throughput and the improvement in the ratio of automation are strongly desired to the SEM device and so on used as the dimensional control tool. The present invention relates to an automatic recipe creation of the SEM device. According to the present invention, it becomes possible to image and measure a number of evaluation points with high ratio of automation, at high speed, and with high accuracy, thus pattern designing of a semiconductor device, and the feed-back to the manufacturing process become possible.

What is claimed is:

1. A method of measuring a dimension of a circuit pattern, which is formed on a substrate, using a scanning electron microscope (SEM), comprising the steps of:
   (a) inputting a center coordinate of an SEM image area and design information of a circuit pattern;
   (b) setting a measurement object area including an edge of the circuit pattern having a dimension to be measured, using the center coordinate of the SEM imaging area and the design information input, and setting an imaging area and imaging condition for imaging an area including the measurement object area with the scanning electron microscope;
   (c) setting an imaging sequence for imaging the imaging area with the scanning electron microscope for measuring the dimension of the circuit pattern;
   (d) imaging the circuit pattern formed on the substrate with the scanning electron microscope based on the imaging condition and the imaging sequence; and
   (e) processing the image obtained by imaging to measure the dimension of the circuit pattern,
   wherein, step (b) includes the steps of setting, as the measurement object area, an area including the edge of the circuit pattern in the vicinity of the position at which the dimension of the circuit pattern is measured, and setting in accordance with a direction of the edge of the circuit pattern included in the area, a direction of continuous scanning of an electron beam scanned in the scanning electron microscope.

2. An apparatus adapted to measure a dimension of a circuit pattern formed on a substrate using a scanning electron microscope, comprising:
   input means for inputting a center coordinate of an SEM image area and design information of a circuit pattern;
   imaging condition setting means including a measurement object area setting section adapted to set a measurement object area including an edge of the circuit pattern having a dimension to be measured, using the center coordinate of the SEM imaging area and the design information input, and an area/condition setting section adapted to set an imaging area and imaging condition for imaging an area including the measurement object area with the scanning electron microscope;
   imaging sequence setting means for setting an imaging sequence for imaging the imaging area, which is set by the imaging condition setting means for measuring the dimension of the circuit pattern, with the scanning electron microscope;
   scanning electron microscope means for imaging the circuit pattern formed on the substrate based on the imaging condition set by the imaging condition setting means and the imaging sequence set by the imaging sequence setting means; and
   image processing means for processing the image obtained by imaging with the scanning electron microscope means to measure the dimension of the circuit pattern,
   wherein, the measurement object area setting section of the imaging condition setting means sets, as an area including a position at which the dimension of the circuit pattern is measured, an area including the edge of the circuit pattern in the vicinity of the position at which the dimension of the circuit pattern is measured, and the imaging condition means further includes a scanning direction setting section adapted to set a direction of continuous scanning of an electron beam scanned in the scanning electron microscope in accordance with a direction of the edge of the circuit pattern included in the area set by the measurement object area setting section.

* * * * *